(12) United States Patent
Müller et al.

(10) Patent No.: US 7,056,941 B1
(45) Date of Patent: Jun. 6, 2006

(54) 2-[PYRAZOLYL AND TRIAZOLYL-3'-OXYMETHYLENE]-PHENYL-ISOXAZOLONES, TRIAZOLONES AND TETRAZOLONES AS PESTICIDES AND FUNGICIDES

(75) Inventors: Bernd Müller, Frankenthal (DE); Hubert Sauter, Mannheim (DE); Herbert Bayer, Mannheim (DE); Markus Gewehr, Kastellaun (DE); Wassilios Grammenos, Ludwigshafen (DE); Thomas Grote, Schifferstadt (DE); Andreas Gypser, Mannheim (DE); Arne Ptock, Ludwigshafen (DE); Reinhard Kirstgen, Neustadt (DE); Norbert Götz, Worms (DE); Roland Götz, Ludwigshafen-Reingönnheim (DE); Franz Röhl, Schifferstadt (DE); Eberhard Ammermann, Heppenheim (DE); Volker Harries, Frankenthal (DE); Gisela Lorenz, Neustadt (DE); Siegfried Strathmann, Limburgerhof (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/462,647

(22) PCT Filed: Jul. 2, 1998

(86) PCT No.: PCT/EP98/04096

§ 371 (c)(1),
(2), (4) Date: Jan. 11, 2000

(87) PCT Pub. No.: WO99/05139

PCT Pub. Date: Feb. 4, 1999

(30) Foreign Application Priority Data

Jul. 21, 1997 (DE) .......... 197 31 153

(51) Int. Cl.
*A01N 43/653* (2006.01)
*C07D 249/12* (2006.01)

(52) U.S. Cl. .......... 514/384; 548/263.2; 548/263.4; 548/263.6; 548/263.8; 548/264.6

(58) Field of Classification Search .......... 514/384; 548/263.2, 263.4, 263.6, 263.8, 264.6
See application file for complete search history.

(56) References Cited

U.S. PATENT DOCUMENTS 5,707,936 A    1/1998    Oberdorf et al.

FOREIGN PATENT DOCUMENTS

CA    2217778    11/1996

(Continued)

OTHER PUBLICATIONS

Cran and Hammond , "Organic Chemistry", McGraw Hill Book Co. , NY (1964) 2nd Edition , pp 565–67.*

(Continued)

*Primary Examiner*—Patricia L. Morris
(74) *Attorney, Agent, or Firm*—Jason D. Voight

(57) ABSTRACT

2-[Pyrazolyl- and triazolyl-3'-oxymethylene] phenylisoxazolones, -triazolones and -tetrazolones of formula I

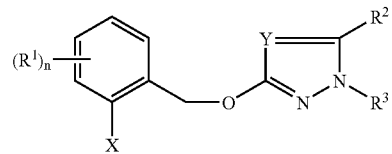

where:
X is a group A, B or C,

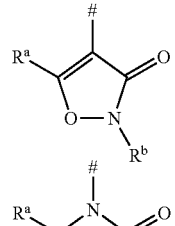

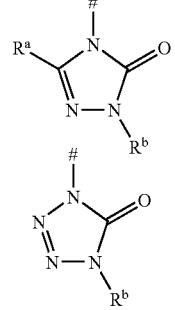

where
\# denotes the bond with the phenyl ring,
$R^a$ is hydrogen, halogen, alkyl or alkoxy,
$R^b$ is alkyl;
Y is N or $CR^c$, where $R^c$ is hydrogen, halogen or alkyl;
n is 0, 1, 2, 3 or 4, where the substituents $R^1$ may be different if n is greater than 1;
$R^1$ is nitro, cyano, halogen, alkyl with or without substitution or alkoxy with or without substitution or is additionally, if n is 2, an optionally substituted 3 or 4 membered bridge which forms together with the ring to which it is attached a bicyclic partially unsaturated or aromatic radical;
$R^2$ is hydrogen, nitro, cyano, halogen, alkyl, haloalkyl, alkoxy, alkylthio or alkoxycarbonyl;
$R^3$ is optionally substituted alkyl, optionally substituted cycloalkyl, optionally substituted aryl or optionally substituted hetaryl,
their preparation and their use for controlling unwanted animal pests or harmful fungi.

16 Claims, No Drawings

FOREIGN PATENT DOCUMENTS

| | | |
|---|---|---|
| WO | 93/15046 | 8/1993 |
| WO | 95/14009 | 5/1995 |
| WO | 96/01256 | 1/1996 |
| WO | 96/01258 | 1/1996 |
| WO | 96/36229 | 11/1996 |
| WO | 97/02255 | 1/1997 |
| WO | 99/33812 * | 7/1999 |

OTHER PUBLICATIONS

Abstract 96/38425 (1995).
Derwent Abstract WO/97/05120 (1997).

* cited by examiner

2-[PYRAZOLYL AND TRIAZOLYL-3'-OXYMETHYLENE]-PHENYL-ISOXAZOLONES, TRIAZOLONES AND TETRAZOLONES AS PESTICIDES AND FUNGICIDES

The present invention relates to 2-[pyrazolyl- and triazolyl-3'-oxymethylene]phenylisoxazolones, -triazolones and -tetrazolones of the formula I

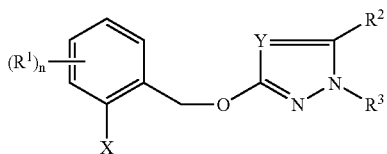

where:
X is a group A, B or C,

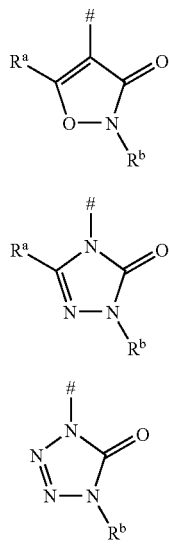

where
# denotes the bond with the phenyl ring and
$R^a$ is hydrogen, halogen, $C_1$–$C_4$-alkyl or $C_1$–$C_4$-alkoxy and
$R^b$ is $C_1$–$C_4$-alkyl;
Y is N or $CR^c$, where
$R^c$ is hydrogen, halogen or $C_1$–$C_4$-alkyl;
n is 0, 1, 2, 3 or 4, where the substituents $R^1$ may be different if n is greater than 1;
$R^1$ is nitro, cyano, halogen,
  $C_1$–$C_6$-alkyl with or without substitution or alkoxy with or without substitution or
  is additionally, if n is 2, a bridge with or without substitution containing 3 to 4 members of the group 3 or 4 carbon atoms, 2 to 3 carbon atoms and 1 or 2 nitrogen, oxygen and/or sulfur atoms which is attached to two adjacent ring atoms, it being possible for this bridge to form together with the ring to which it is attached a partially unsaturated or aromatic radical;
$R^2$ is hydrogen, nitro, cyano, halogen, $C_1$–$C_4$-alkyl, $C_1$–$C_4$haloalkyl, $C_1$–$C_4$alkoxy, $C_1$–$C_4$alkylthio or $C_1$–$C_4$alkoxycarbonyl;

$R^3$ is $C_1$–$C_6$-alkyl with or without substitution, $C_3$–$C_6$cycloalkyl with or without substitution, aryl with or without substitution or hetaryl with or without substitution.

Additionally, the invention relates to processes for preparing these compounds, to compositions comprising them and to their use for controlling animal pests or harmful fungi.

WO-A 93/15046, WO-A 96/01256 and WO-A 96/01258 disclose 2-[pyrazolyl-4-oxymethylene]anilides and 2-[triazolyl-4-oxymethylene]anilides for controlling animal pests and harmful fungi.

WO-A 95/14009, WO-A 96/36229, WO-A 96/38425, WO-A 97/05120 and WO-A 97/02255 disclose 4-phenyl-2,3-dihydroisoxazolones, 4-phenyl-2,4-dihydrotriazolones and 2-phenyl-2,5-dihydrotetrazolones having substituents in the ortho position of the phenyl radical.

It is an object of the present invention to provide compounds having an improved activity.

We have found that this object is achieved by the compounds defined at the outset. In addition, the invention provides processes for preparing them, compositions comprising them and methods for controlling animal pests and harmful fungi using the compounds I.

The compounds of the formula I differ from those disclosed in the abovementioned publications WO-A 93/15046, WO-A 96/01256 and WO-A 96/01258 in the isoxazolone, triazolone or tetrazolone radical at the phenyl ring, and they differ from the compounds disclosed in WO-A 95/14009, WO-A 96/36229, WO-A 96/38425, WO-A 97/05120 and WO-A 97/02255 in the oxymethylenepyrazolyl or oxymethylenetriazolyl group at the phenyl ring. Compared with the prior art compounds, the compounds of the formula I have increased activity against harmful fungi and animal pests.

The compounds of the formula I can be obtained per se by a method similar to the methods described in WO-A 95/14009, WO-A 96/01256, WO-A 96/01258, WO-A 96/36229, WO-A 96/38425, WO-A 97/05120, or WO-A 97/02255.

The compounds I can be obtained by various routes, it being immaterial for the synthesis whether the group X or the pyrazolyl or triazolyl group is built up first. For clarity, the term $X^\#$ is therefore used for the radical X or a suitable precursor of this radical and the term $E^\#$ is used for the pyrazolyl or triazolyl group or a suitable precursor thereof in the descriptions of the reactions hereinbelow.

The compounds I are obtained, for example, by converting a benzyl derivative of the formula $II^\#$ in the presence of a base with a 3-hydroxypyrazole or 3-hydroxytriazole of the formula III into the corresponding phenyl derivative of the formula $V^\#$.

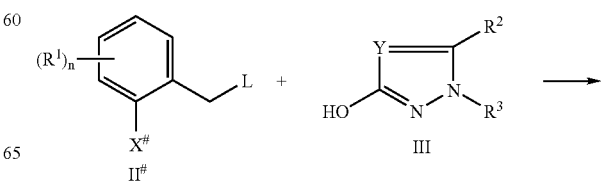

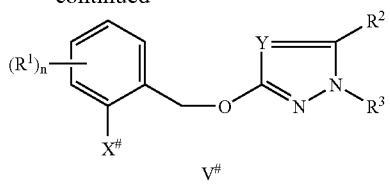

If the radical $X^\#$ in the formula $V^\#$ is a group A, B or C, the phenyl compounds of the formula $V^\#$ correspond to those of the formula I.

In the formula II, L is a nucleophilically displaceable group, for example halogen (eg. chlorine, bromine and iodine), or an alkyl or aryl sulfonate (eg. methylsulfonate, trifluoromethylsulfonate, phenylsulfonate and 4-methylphenylsulfonate).

The etherification of the compounds $II^\#$ and III is usually carried out at from 0° C. to 80° C., preferably from 20° C. to 60° C.

Suitable solvents are aromatic hydrocarbons such as toluene, o-, m- and p-xylene, halogenated hydrocarbons such as methylene chloride, chloroform and chlorobenzene, ethers such as diethyl ether, diisopropyl ether, tert-butyl methyl ether, dioxane, anisol and tetrahydrofuran, nitriles such as acetonitrile and propionitrile, alcohols such as methanol, ethanol, n-propanol, i-propanol, n-butanol and tert-butanol, ketones such as acetone and methyl ethyl ketone and dimethyl sulfoxide, dimethylformamide, dimethylacetamide, 1,3-dimethylimidazolidin-2-one and 1,2-dimethyltetrahydro-2(1H)-pyrimidine, preferably methylene chloride, acetone, toluene, methyl tert-butyl ether and dimethylformamide. Mixtures of the solvents mentioned can also be employed.

In general, suitable bases are inorganic compounds such as alkali metal and alkaline earth metal hydroxides (eg. lithium hydroxide, sodium hydroxide, potassium hydroxide and calcium hydroxide), alkali metal and alkaline earth metal oxides (eg. lithium oxide, sodium oxide, calcium oxide and magnesium oxide), alkali metal and alkaline earth metal hydrides (eg. lithium hydride, sodium hydride, potassium hydride and calcium hydride), alkali metal amides (eg. lithium amide, sodium amide and potassium amide), alkali metal and alkaline earth metal carbonates (eg. lithium carbonate and calcium carbonate) and alkali metal bicarbonates (eg. sodium bicarbonate), organometallic compounds, in particular alkali metal alkyls (eg. methyllithium, butyllithium and phenyllithium), alkylmagnesium halides (eg. methylmagnesium chloride) and alkali metal and alkaline earth metal alkoxides (eg. sodium methoxide, sodium ethoxide, potassium ethoxide, potassium tert-butoxide and dimethoxymagnesium), moreover organic bases, eg. tertiary amines such as trimethylamine, triethylamine, triisopropylethylamine and n-methylpiperidine, pyridine, substituted pyridines such as collidine, lutidine and 4-dimethylamino pyridine, and also bicyclic amines. Particular preference is given to sodium hydroxide, potassium carbonate and potassium tert-butoxide. In general, the bases are employed in equimolar amounts, in an excess or, if appropriate, as solvent.

It may be advantageous for the reaction to add a catalytic amount of a crown ether (eg. 18-crown-6 or 15-crown-5).

It is also possible to carry out the reaction in a two-phase system comprising a solution of alkali metal or alkaline earth metal hydroxides or carbonates in water and an organic phase (eg. aromatic and/or halogenated hydrocarbons). Phase-transfer catalysts which are suitable for this purpose are for example ammonium halides and ammonium tetrafluoroborates (eg. benzyltriethylammonium chloride, benzyltributylammonium bromide, tetrabutylammonium chloride, hexadecyltrimethylammonium bromide or tetrabutylammonium tetrafluoroborate) and phosphonium halides (eg. tetrabutylphosphonium chloride and tetrabutylphosphonium bromide).

It may be advantageous for the reaction to convert initially the 3-hydroxypyrazole with the base into the corresponding hydroxylate which is then reacted with the benzyl derivative.

The benzyl compounds $II^\#$ required for preparing the compounds I are disclosed in the literature [cf. WO-A 95/14009; WO-A 96/36229; WO-A 97/02255]. They can be obtained by the following synthetic route:

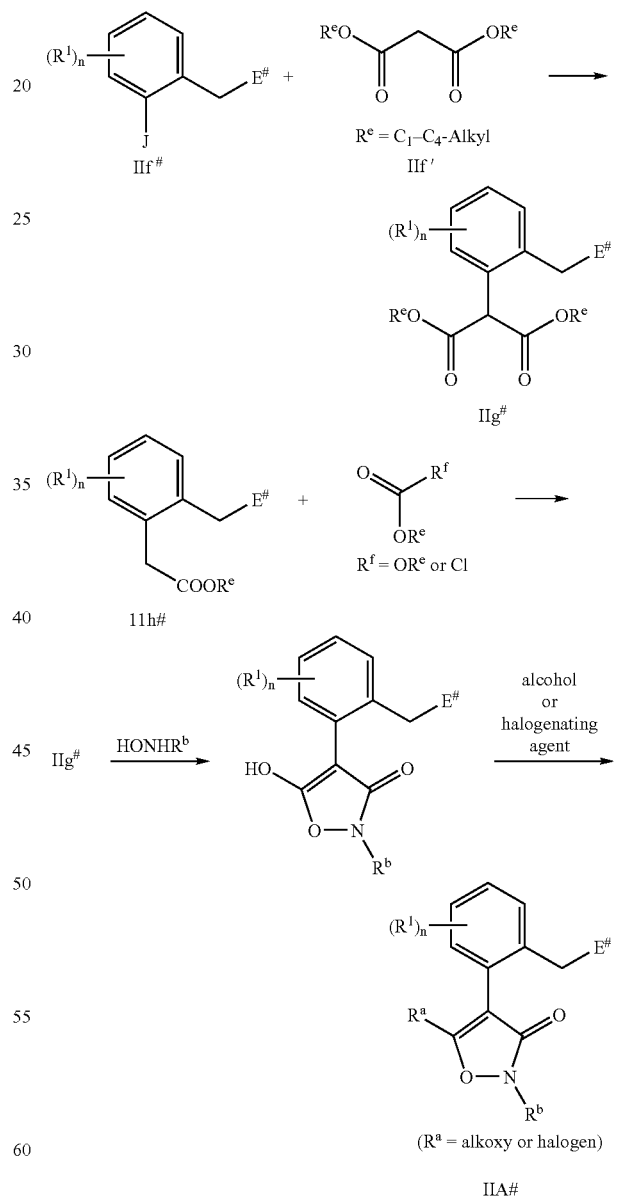

Compounds of the formula $IIA^\#$ in which $R^a$ is alkyl are obtained from the corresponding phenylacetic esters $IIh^\#$ by the routes known from U.S. Pat. No. 4,952,573 and WO-A 96/36229.

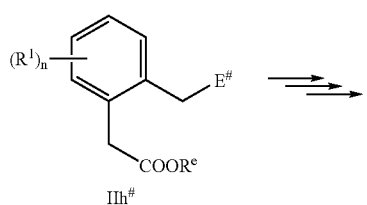

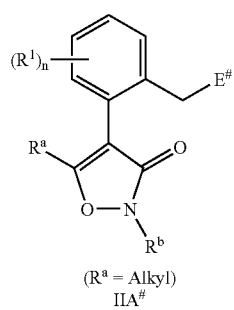

Compounds of the formula IIB# are obtainable by the following synthesis route [cf. WO-A 95/14009; WO-A 96/36229; WO-A 97/02255]:

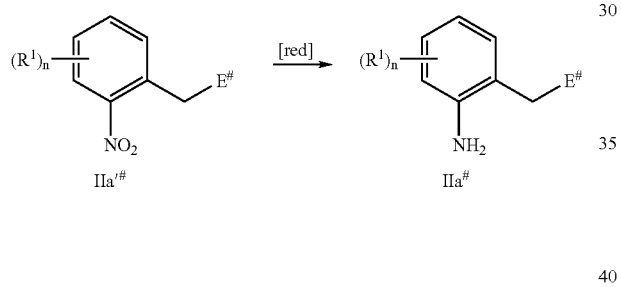

The nitro group of IIa'# can be reduced under generally customary conditions, preferably by catalytic hydrogenation, by reduction with iron, tin or zinc in the presence of an acid, by reduction with alkali metals in the presence of a base or by enzyme-catalyzed reduction [cf. Houben-Weyl, vol. IV/1c, 4th edition, p. 506 ff., Thieme Verlag Stuttgart and New York (1980); ibid. vol. IV/1d, 4th edition, p. 473 ff. (1981); Heterocycles, vol. 31, p. 2201 (1990)]

Some nitrobenzene derivatives of the formula IIa'[190] are known from the literature [cf. WO-A 93/15046; WO-A 95/14009], or they can be prepared in accordance with the literature cited.

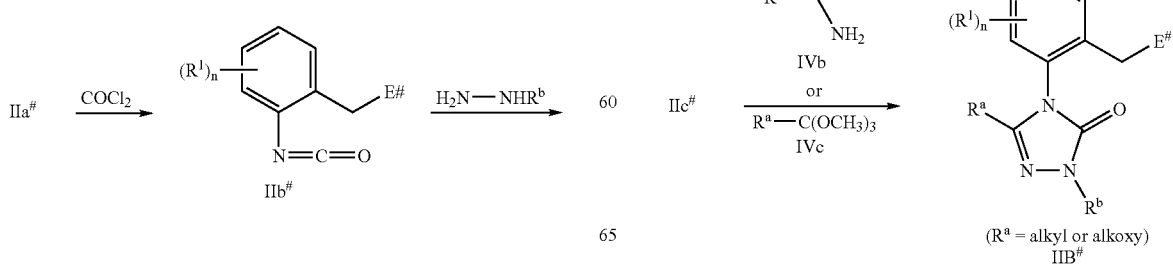

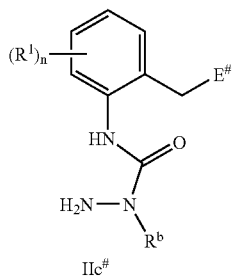

The reaction of IIa[190] with phosgene or a phosgene equivalent, such as, for example, di- or triphosgene or phenyl chloroformate, is usually carried out at from −10° C. to 250° C., preferably 10° C. to 110° C., in an inert organic solvent in the presence of a base or a catalyst [cf. Chem. Ber., vol. 72, p. 457 (1972); Chem. Soc. Rev., vol. 3, p. 209 (1974); Angew. Chem., vol. 107, p. 2746 (1995)].

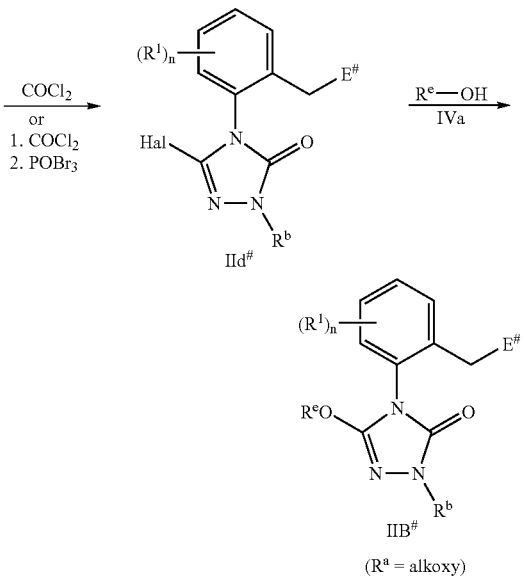

In the formula IId# "Hal" is a halogen atom, such as chlorine or bromine.

The benzyl compounds IIB# required for preparing the compounds IB in which $R^a$ is alkyl or alkoxy are also known from the literature [cf. WO-A 96/36229], or they can be obtained by literature methods [cf. J. Org. Chem., vol. 43 (1978) p. 936]. They can be obtained by reaction of the carbamates of the formula IIc# with amidines IVb or orthoesters IVc:

Compounds of the formula IIC# can be obtained by the following synthesis route [cf. WO-A 95/14009; WO-A 96/36229; WO-A 97/02255]:

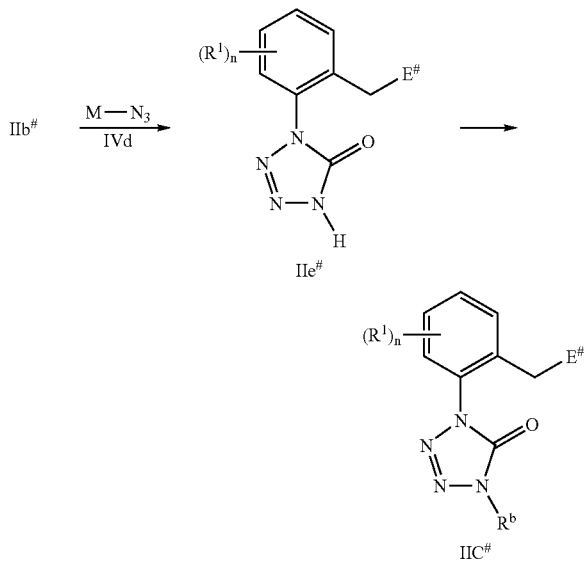

The reaction of the isocyanates IIb# with the azides IVd is usually carried out at from −10° C. to 200° C., preferably at from 20° C. to 140° C., in an inert organic solvent, if appropriate in the presence of a base or an acid [cf. J. Org. Chem., vol. 45, p. 5130 (1980); J. Am. Chem. Soc., vol. 81, p., 3076 (1959); Tetrahedron, vol. 31, p. 765 (1975); J. Org. Chem., vol. 38, p. 675 (1973)].

In the formula IVd, M is a cation from the group of the alkali or alkaline earth metals, trialkylsilyl or alkyl. Preference is given to using trimethylsilyl azide.

The alkylation of the tetrazolinones IIe# to give IIC# is usually carried out at from −20° C. to 180° C., preferably at from 20° C. to 120° C., in an inert organic solvent in the presence of a base [cf. Synth. Commun., vol. 18, p. 2011 (1988); J. Chem. Soc. Chem. Commun., p. 735 (1987)].

Suitable alkylating agents are, for example, alkyl halides, alkylsulfonates, alkyl-p-toluenesulfonates, alkyltrifluoromethanesulfonates, alcohols, dialkyl ethers or alkyl-p-bromophenylsulfonates, in particular methyl iodide or dimethyl sulfate.

If E# in the formulae IIA#, IIb# and IIC# is the pyrazole or the triazole group, the compounds IIA#, IIB# and IIC# correspond to the compounds IA, IB and IC, respectively.

These syntheses are not only suitable for preparing the benzyl compounds II#, but can be used in principle at each stage of the synthesis of the pyrazole or triazole group for building up the groups A, B or C. The synthesis of the group X is particularly preferably carried out at the stage of the compounds IIa'1# or IIb# in which E# is hydrogen or the pyrazole or triazole group. 3-Hydroxypyrazoles IIIa are also disclosed in the literature, or they can be prepared by the methods described therein [J. Heterocycl. Chem. 30, (1993), 49, Chem. Ber. 107, (1974), 1318, Chem. Pharm. Bull. 19, (1971), 1389, Tetrahedron Lett. 11, (1970), 875, Chem. Heterocycl. Comp. 5, (1969), 527, Chem. Ber. 102, (1969), 3260, Chem. Ber. 109, (1976), 261, J. Org. Chem. 31, (1966), 1538, Tetrahedron 43, (1987), 607].

The 3-hydroxypyrazoles IIIa are particularly advantageously obtained by the processes described in WO-A 97/03969 and DE Appl. No. 19 652 516.0.

3-Hydroxytriazoles IIIb are also disclosed in the literature, or they can be prepared by the methods described therein [Chem. Ber. 56, (1923), 1794; DE-A 21 50 169; DE-A 22 00 436; U.S. Pat. No. 4,433,148; J. Med. Chem. 33, (1990), 2772; Synthesis 1987, 986; DE-A 22 60 015; DE-A 24 17 970].

The reaction mixtures are worked up in a customary manner, for example by mixing with water, separation of the phases and, if appropriate, chromatographic purification of the crude products. Some of the intermediates and end products are obtained in the form of colorless or slightly brownish, viscous oils, which are freed from volatile components or purified under reduced pressure and at moderately elevated temperature. If the intermediates and end products are obtained as solids, purification can also be carried out by recrystallization or digestion.

The compounds I may contain acidic or basic centers and may thus be able to form acid addition products or base addition products or salts.

Acids for acid addition products are inter alia mineral acids (eg. hydrohalic acids such as hydrochloric acid and hydrobromic acid, phosphoric acid, sulfuric acid, nitric acid), organic acids (eg. formic acid, acetic acid, oxalic acid, malonic acid, lactic acid, malic acid, succinic acid, tartaric acid, citric acid, salicylic acid, p-toluenesulfonic acid, dodecylbenzenesulfonic acid) or other proton-acidic compounds (eg. saccharin). Bases for base addition products are inter alia oxides, hydroxides, carbonates or bicarbonates of alkali metals or alkaline earth metals (eg. potassium hydroxide, sodium hydroxide, potassium carbonate or sodium carbonate) or ammonium compounds (eg. ammonium hydroxide).

In some of the symbol definitions given in the formulae above, collective terms were used which generally represent the following substituents:

Halogen: fluorine, chlorine, bromine and iodine;

Alkyl: saturated, straight-chain or branched hydrocarbon radicals having 1 to 4 or 6 carbon atoms, eg. methyl, ethyl, propyl, 1-methylethyl, butyl, 1-methylpropyl, 2-methylpropyl and 1,1-dimethylethyl;

Haloalkyl: straight-chain or branched alkyl groups having 1 to 4 carbon atoms (as mentioned above), it being possible for the hydrogen atoms in these groups to be partly or wholly replaced by halogen atoms as mentioned above, eg. $C_1$–$C_2$-haloalkyl such as chloromethyl, dichloromethyl, trichloromethyl, fluoromethyl, difluoromethyl, trifluoromethyl, chloroflubromethyl, dichlorofluoromethyl, chlorodifluoromethyl, 1-fluoroethyl, 2-fluoroethyl, 2,2-difluoroethyl, 2,2,2-tri-fluoroethyl, 2-chloro-2-fluoroethyl, 2-chloro-2,2-difluoroethyl, 2,2-dichloro-2-fluoroethyl, 2,2,2-trichloroethyl and pentafluoroethyl;

Alkylcarbonyl: straight-chain or branched alkyl groups, in particular those having 1 to 10 carbon atoms (as mentioned above), which are attached to the skeleton via a carbonyl group (—CO—);

Alkoxy: straight-chain or branched alkyl groups having 1 to 4 carbon atoms (as mentioned above), which are attached to the skeleton via an oxygen atom (—O—);

Alkoxycarbonyl: straight-chain or branched alkoxy groups having 1 to 4 carbon atoms (as mentioned above), which are attached to the skeleton via a carbonyl group (—CO—);

Alkylthio: straight-chain or branched alkyl groups having 1 to 4 carbon atoms (as mentioned above), which are attached to the skeleton via a sulfur atom (—S—);

Cycloalkyl: monocyclic, saturated hydrocarbon groups having 3 to 6 carbon ring members, eg. cyclopropyl, cyclobutyl, cyclopentyl and cyclohexyl;

Aryl: a mono- to three-nuclear aromatic ring system containing 6 to 14 carbon ring members, eg. phenyl, naphthyl and anthracenyl;

Hetaryl: 5- or 6-membered heteroaromatics, eg.

5-membered hetaryl containing one to four nitrogen atoms or one to three nitrogen atoms and one sulfur or oxygen atom: 5-membered ring hetaryl groups which may, in addition to carbon atoms, contain one to four nitrogen atoms or one to three nitrogen atoms and one sulfur or oxygen atom as ring members, eg. 2-furyl, 3-furyl, 2-thienyl, 3-thienyl, 2-pyrrolyl, 3-pyrrolyl, 3-isoxazolyl, 4-isoxazolyl, 5-isoxazolyl, 3-isothiazolyl, 4-isothiazolyl, 5-isothiazolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 2-imidazolyl, 4-imidazolyl, 1,2,4-oxadiazol-3-yl, 1,2,4-oxadiazol-5-yl, 1,2,4-thiadiazol-3-yl, 1,2,4-thiadiazol-5-yl, 1,2,4-triazol-3-yl, 1,3,4-oxadiazol-2-yl, 1,3,4-thiadiazol-2-yl and 1,3,4-triazol-2-yl;

benzofused 5-membered hetaryl containing one to three nitrogen atoms or one nitrogen atom and one oxygen or sulfur atom: 5-membered ring hetaryl groups which may, in addition to carbon atoms, contain one to four nitrogen atoms or one to three nitrogen atoms and one sulfur or oxygen atom as ring members, and in which two neighboring carbon ring members or one nitrogen and one neighboring carbon ring member may be bridged by a buta-1,3-diene-1,4-diyl group;

5-membered hetaryl which is attached via nitrogen and contains one to four nitrogen atoms, or benzofused 5-membered hetaryl which is attached via nitrogen and contains one to three nitrogen atoms: 5-membered ring hetaryl groups which may, in addition to carbon atoms, contain one to four nitrogen atoms or one to three nitrogen atoms as ring members, and in which two neighboring carbon ring members or one nitrogen and one neighboring carbon ring member may be bridged by a buta-1,3-diene-1,4-diyl group, these rings being attached to the skeleton via one of the nitrogen ring members;

6-membered hetaryl containing one to three or one to four nitrogen atoms: 6-membered ring hetaryl groups which may, in addition to carbon atoms, contain one to three or one to four nitrogen atoms as ring members, eg. 2-pyridinyl, 3-pyridinyl, 4-pyridinyl, 3-pyridazinyl, 4-pyridazinyl, 2-pyrimidinyl, 4-pyrimidinyl, 5-pyrimidinyl, 2-pyrazinyl, 1,3,5-triazin-2-yl and 1,2,4-triazin-3-yl;

With respect to alkyl, alkenyl and alkynyl groups, the term "with or without substitution" is intended to express that these groups may be partially or fully halogenated (ie. the hydrogen atoms of these groups may be partly or wholly replaced by identical or different halogen atoms as mentioned above (preferably fluorine, chlorine and bromine, in particular fluorine and chlorine) and/or carry one to three, in particular one, of the following radicals: $C_1$–$C_6$-alkoxy, $C_1$–$C_6$-haloalkoxy, $C_1$–$C_6$-alkylthio, $C_1$–$C_6$haloalkylthio, $C_1$–$C_6$-alkylamino, di-($C_1$–$C_6$)-alkylamino, $C_2$–$C_6$-alkenyloxy, $C_2$–$C_6$-haloalkenyloxy, $C_2$–$C_6$-alkynyloxy, $C_2$–$C_6$haloalkynyloxy, $C_3$–$C_6$-cycloalkyl, $C_3$–$C_6$-cycloalkyloxy, $C_3$–$C_6$cycloalkenyl, $C_3$–$C_6$-cycloalkenyloxy, or a mono- or dinuclear aromatic ring system with or without substitution which may, in addition to carbon atoms, contain one to four nitrogen atoms or one or two nitrogen atoms and one oxygen or sulfur atom or one oxygen or may be sulfur atom as ring members (as mentioned above) and which directly or attached to the substituent an oxygen atom (—O—), a sulfur atom (—S—) or via an amino group (—NR$^a$—), ie. aryl radicals such as phenyl and naphthyl, preferably phenyl or 1- or 2-naphthyl, and hetaryl radicals, for example 5-membered ring heteroaromatics containing one to three nitrogen atoms and/or one oxygen or sulfur atom such as 2-furyl, 3-furyl, 2-thienyl, 3-thienyl, 1-pyrrolyl, 2-pyrrolyl, 3-pyrrolyl, 3-isoxazolyl, 4-isoxazolyl, 5-isoxazolyl, 3-isothiazolyl, 4-isothiazolyl, 5-isothiazolyl, 1-pyrazolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 1-imidazolyl, 2-imidazolyl, 4-imidazolyl, 1,2,4-oxadiazol-3-yl, 1,2,4-oxadiazol-5-yl, 1,2,4-thiadiazol-3-yl, 1,2,4-thiadiazol-5-yl, 1,2,5-triazol-3-yl, 1,2,3-triazol-4-yl, 1,2,3-triazol-5-yl, 1,2,3-triazol-4-yl, 5-tetrazolyl, 1,2,3,4-thiatriazol-5-yl and 1,2,3,4-oxatriazol-5-yl, in particular 3-isoxazolyl, 5-isoxazolyl, 4-oxazolyl, 4-thiazolyl, 1,3,4-oxadiazol-2-yl and 1,3,4-thiadiazol-2-yl;

Six-membered ring heteroaromatics containing one to four nitrogen atoms as hetero atoms such as 2-pyridinyl, 3-pyridinyl, 4-pyridinyl, 3-pyridazinyl, 4-pyridazinyl, 2-pyrimidinyl, 4-pyrimidinyl, 5-pyrimidinyl, 2-pyrazinyl, 1,3,5-triazin-2-yl, 1,2,4-triazin-3-yl and 1,2,4,5-tetrazin-3-yl, in particular 2-pyridinyl, 3-pyridinyl, 4-pyridinyl, 2-pyrimidinyl, 4-pyrimidinyl, 2-pyrazinyl and 4-pyridazinyl.

With respect to the cyclic (saturated, unsaturated or aromatic) groups, the term "with or without substitution" is intended to express that these groups may be partially or fully halogenated [ie. the hydrogen atoms of these groups may be partly or wholly replaced by identical or different halogen atoms as mentioned above (preferably fluorine, chlorine or bromine, in particular fluorine or chlorine)] and/or carry one to four (in particular one to three) of the following radicals:

cyano, nitro, hydroxy, amino, carboxyl, aminocarbonyl, alkyl, haloalkyl, alkenyl, haloalkenyl, alkenyloxy, haloalkenyloxy, alkynyl, haloalkynyl, alkynyloxy, ;haloalkynyloxy, alkoxy, haloalkoxy, alkylthio, haloalkylthio, alkylamino, dialkylamino, alkylcarbonyl, alkoxycarbonyl, alkylcarbonyloxy, alkylaminocarbonyl, dialkylaminocarbonyl, alkylcarbonylamino, alkokycarbonylamino, alkylcarbonyl-N-alkylamino and alkoxycarbonyl-N-alkylamino, where the alkyl groups in these radicals preferably contain 1 to 6 carbon atoms, in particular 1 to 4 carbon atoms and where the mentioned alkenyl or alkynyl groups in these radicals contain 2 to 8, preferably 2 to 6, in particular 2 to 4 carbon atoms;

and/or one to three (in particular one) of the following radicals:

cycloalkyl, cycloalkoxy, cycloalkylthio, cycloalkylamino, cycloalkyl-N-alkylamino, heterocyclyl, heterocyclyloxy, heterocyclylthio, heterocyclylamino or heterocyclyl-N-alkylamino, without substitution or with substitution by customary groups, where the cyclic systems contain 3 to 12 ring members, preferably 2 to 8 ring members, in particular 3 to 6 ring members, and the alkyl groups in these radicals preferably contain 1 to 6 carbon atoms, in particular 1 to 4 carbon atoms;

aryl, aryloxy, arylthio, arylamino, aryl-N-alkylamino, arylalkoxy, arylalkylthio, arylalkylamino, arylalkyl-N-alkylamino, hetaryl, hetaryloxy, hetarylthio, hetarylamino, hetaryl-N-alkylamino, hetarylalkoxy, hetarylalkylthio, hetarylalkylamino and hetarylalkyl-N-alkylamino, without substitution or with substitution by customary groups, where the aryl radicals preferably contain 6 to 10 ring members, in particular 6 ring members (phenyl), the hetaryl radicals in particular contain 5 or 6 ring members and the alkyl groups in these radicals preferably contain 1 to 6 carbon atoms, in particular 1 to 4 carbon atoms and/or one or two (in particular one) of the following radicals:

formyl, $CR^{iii}=NOR^{iv}$ [where $R^{iii}$ is hydrogen, alkyl, cycloalkyl and aryl and $R^{iv}$ is alkyl, alkenyl, haloalkenyl, alkynyl and arylalkyl (where the alkyl groups mentioned preferably contain 1 to 6 carbon atoms, in particular 1 to 4 carbon atoms, the cycloalkyl groups, alkenyl groups and alkynyl groups mentioned preferably contain 3 to 8, in particular 3 to 6, carbon atoms) and aryl is in particular phenyl without substitution or with substitution by customary groups] or $NR^v$—CO—D—$R^{vi}$ [where $R^v$ is hydrogen, hydroxy, $C_1$–$C_6$-alkyl, $C_2$–$C_6$-alkenyl, $C_2$–$C_6$-alkynyl, $C_1$–$C_6$-alkoxy, $C_2$–$C_6$-alkenyloxy, $C_2$–$C_6$-alkynyloxy, $C_1$–$C_6$-alkoxy-$C_1$–$C_6$-alkyl, $C_1$–$C_6$-alkoxy-$C_1$–$C_6$-alkoxy and $C_1$–$C_6$-alkoxycarbonyl, $R^{vi}$ is hydrogen, $C_1$–$C_6$-alkyl, $C_2$–$C_6$-alkenyl, $C_2$–$C_6$-alkynyl, $C_3$–$C_6$-cycloalkyl, $C_3$–$C_6$-cycloalkenyl, aryl, aryl-$C_1$–$C_6$-alkyl, hetaryl and hetaryl-$C_1$–$C_6$-alkyl and D is a direct bond, oxygen or nitrogen, where the nitrogen may carry one of the groups mentioned under $R^{vi}$], and/or where two neighboring C-atoms of the cyclic systems may carry a $C_3$–$C_5$-alkylene, $C_3$–$C_5$-alkenylene, oxy-$C_2$–$C_4$-alkylene, oxy-$C_1$–$C_3$-alkylenoxy, oxy-$C_2$–$C_4$-alkenylene, oxy-$C_2$–$C_4$-alkenylenoxy or butadienediyl group, where these bridges in turn may be partially or fully halogenated and/or may carry one to three, in particular one or two, of the following radicals:

$C_1$–$C_4$-alkyl, $C_1$–$C_4$-haloalkyl, $C_1$–$C_4$-alkoxy, $C_1$–$C_4$-haloalkoxy and $C_1$–$C_4$-alkylthio.

With respect to their biological activity, preference is given to compounds IA.

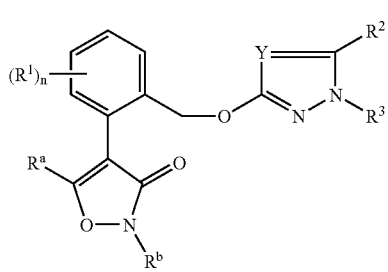

In addition, preference is also given to compounds of the formula IB.

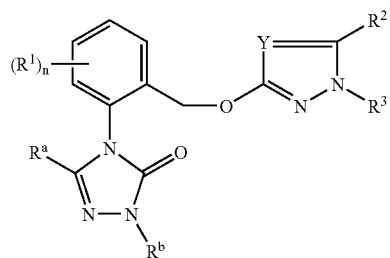

Likewise, preference is given to compounds IC.

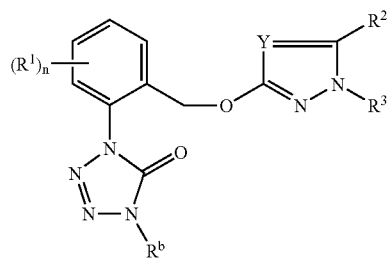

Furthermore, preference is given to compounds I in which $R^a$ is methoxy.

Additionally, preference is also given to compounds I in which $R^a$ is methyl.

Furthermore, preference is also given to compounds I in which $R^b$ is methyl.

Likewise, preference is given to compounds I in which n is 0 or 1, in particular 0.

In addition, preference is given to compounds I in which $R^1$ is in position 6.

Furthermore, preference is given to compounds I in which $R^1$ is halogen or methyl.

Likewise, preference is given to compounds I in which $R^2$ is hydrogen.

Additionally, preference is given to compounds I in which $R^3$ is $C_1$–$C_6$-alkyl with or without substitution.

In particular, preference is given to compounds I in which $R^3$ is phenyl or benzyl, it being possible for the phenyl radical to be partially or fully halogenated and/or to carry one to three of the following radicals: cyano, nitro, $C_1$–$C_6$-alkyl, $C_1$–$C_4$-haloalkyl, $C_1$–$C_4$-alkoxy, $C_1$–$C_4$-haloalkoxy, $C_1$–$C_4$-alkoxy-$C_1$–$C_4$-alkyl, $C_3$–$C_6$-cycloalkyl, $C_1$–$C_4$-alkylcarbonyl, $C_1$–$C_4$-alkoxycarbonyl, phenyl, phenoxy and phenyl-$C_1$–$C_4$-alkoxy, where the phenyl rings in turn may be partially or fully halogenated and/or carry one to three of the following radicals: cyano, nitro, $C_1$–$C_4$-alkyl, $C_1$–$C_2$-haloalkyl, $C_1$–$C_4$-alkoxy, $C_1$–$C_2$-haloalkoxy, $C_3$–$C_6$-cycloalkyl, $C_1$–$C_4$-alkylcarbonyl or $C_1$–$C_4$-alkoxycarbonyl, and/or a group CR'=NOR" in which R' is hydrogen or $C_1$–$C_4$-alkyl and R" is $C_1$–$C_6$-alkyl, and/or two neighboring C-atoms of the phenyl ring may be linked by an oxy-$C_1$–$C_3$-alkoxy bridge or an oxy-$C_1$–$C_3$-haloalkoxy bridge.

can carry. [sic]

Furthermore, particular preference is given to compounds I in which $R^3$ is pyridyl, where the pyrydyl ring may be partially or fully halogenated and/or may carry one to three of the following radicals: cyano, nitro, $C_1$–$C_4$-alkyl, $C_1$–$C_2$-haloalkyl, $C_1$–$C_4$-alkoxy, $C_1$–$C_2$-haloalkoxy, $C_3$–$C_6$-cycloalkyl, $C_1$–$C_4$-alkylcarbonyl or $C_1$–$C_4$-alkoxycarbonyl.

In addition, preference is given to compounds I in which $R^b$ is hydrogen.

Moreover, particular preference is given to compounds IA.1, IA.2, IA.3 and IA.4 in which $(R^1)n$ is hydrogen, 6-chloro or 6-methyl, $R^2$ is hydrogen or methyl and $R^3$ is cyclohexyl, benzyl, phenyl, pyridyl or pyrazinyl with or without substitution by halogen or $C_1$–$C_4$-haloalkyl.

is pyridyl, $C_1$–$C_4$-alkoxycarbonyl, methoxymethyl or a group $C(CH_3)=N-C_1-C_4$-alkoxy and the index m is 1–5, in particular 1 or 2.

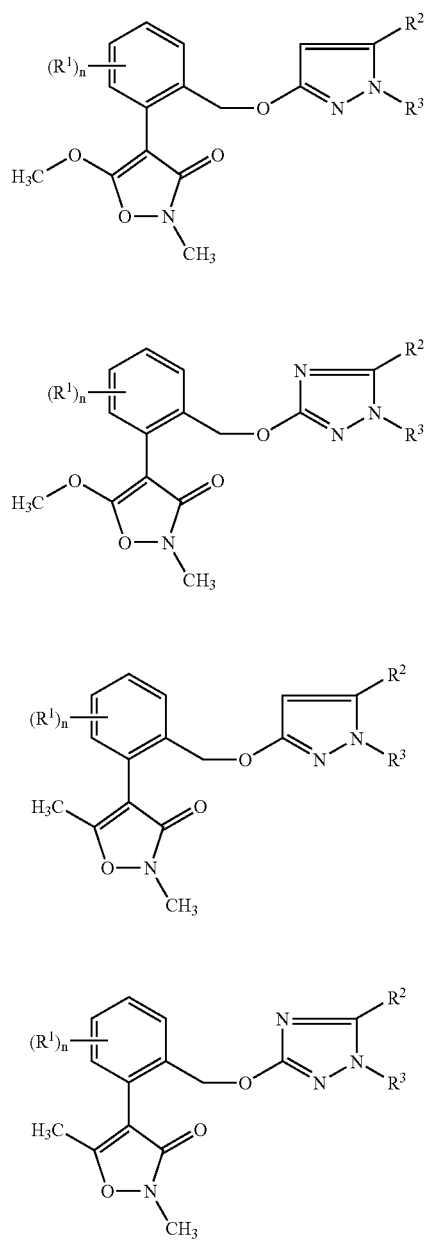

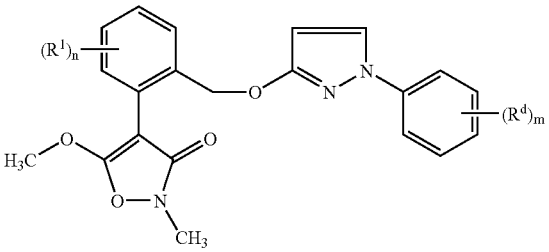

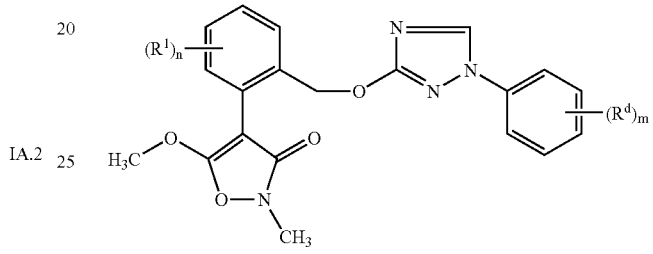

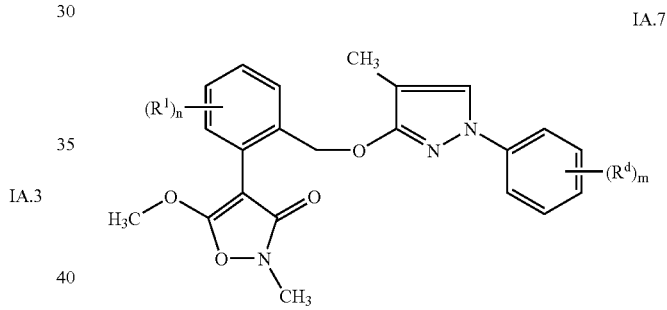

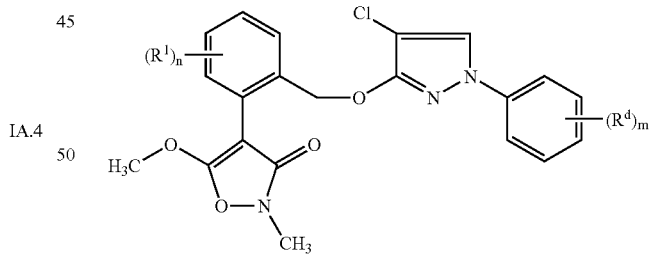

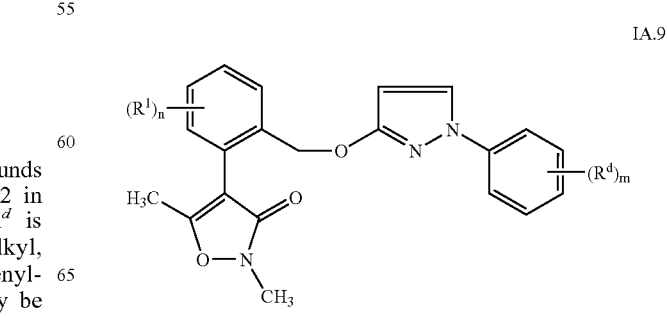

In addition, particular preference is given to compounds IA.5, IA.6, IA.7, IA.8, IA.9, IA.10, IA.11 and IA.12 in which $(R^1)_n$ is hydrogen, 6-chloro or 6-methyl, $R^d$ is halogen, nitro, cyano, $C_1$–$C_9$-alkyl, $C_1$–$C_2$-haloalkyl, cyclohexyl, $C_1$–$C_6$-alkoxy, $C_1$–$C_2$-haloalkoxy, phenyl-$C_1$–$C_3$-alkoxy or phenyl where the phenyl rings may be unsubstituted or substituted by halogen, methyl or methoxy, IA.10
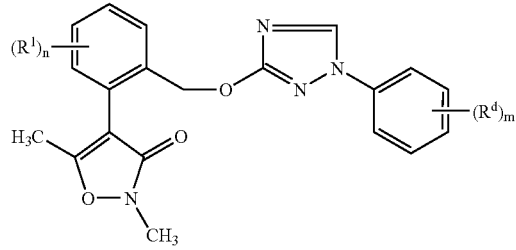

IA.11
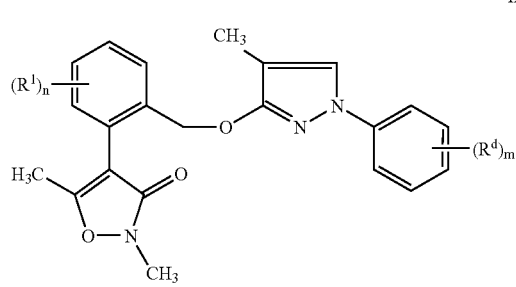

IA.12
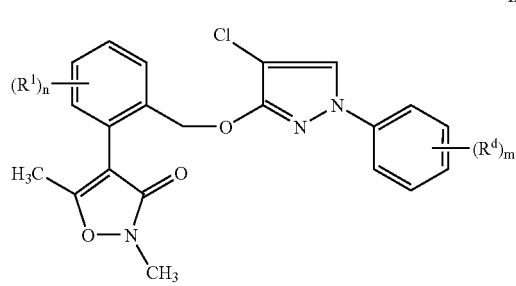

Particular preference is also given in particular to compounds IB.1, IB.2, IB.3 and IB.4 in which $(R^1)$ n is hydrogen, 6-chloro or 6-methyl, $R^2$ is hydrogen or methyl and $R^3$ is cyclohexyl, benzyl, phenyl, pyridyl or pyrazinyl without substitution or with substitution by halogen or $C_1$–$C_4$-haloalkyl.

IB.1
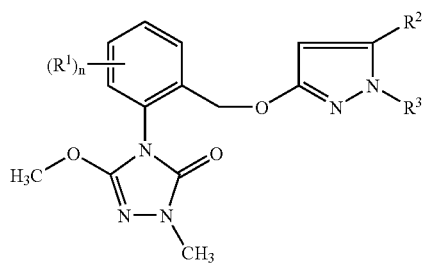

IB.2
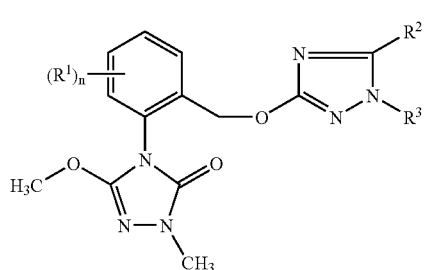

IB.3
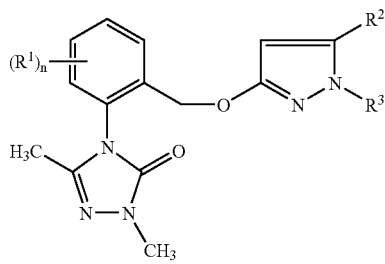

IB.4
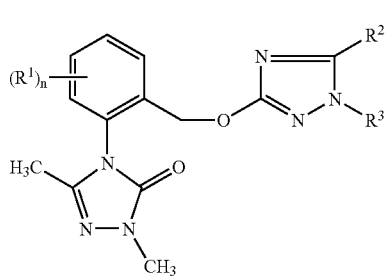

Moreover, particular preference is given to compounds IB.5, IB.6, IB.7, IB.8, IB.9, IB.10, IB.11 and IB.12 in which $(R^1)_n$ is hydrogen, 6-chloro or 6-methyl, $R^d$ is halogen, nitro, cyano, $C_1$–$C_9$-alkyl, $C_1$–$C_2$-haloalkyl, cyclohexyl, $C_1$–$C_6$-alkoxy, $C_1$–$C_2$-haloalkoxy, phenyl-$C_1$–$C_3$-alkoxy or phenyl where the phenyl rings may be unsubstituted or substituted by halogen, methyl or methoxy, is pyridyl, $C_1$–$C_4$-alkoxycarbonyl, methoxymethyl or a group $C(CH_3)=N-C_1$–$C_4$-alkoxy and the index m is 1–5, in particular 1 or 2.

IB.5
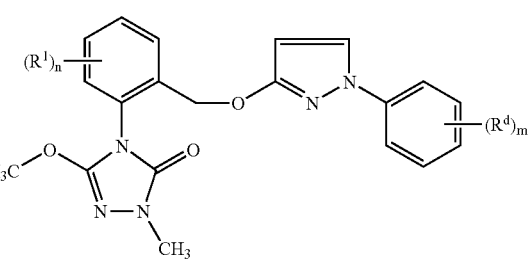

IB.6
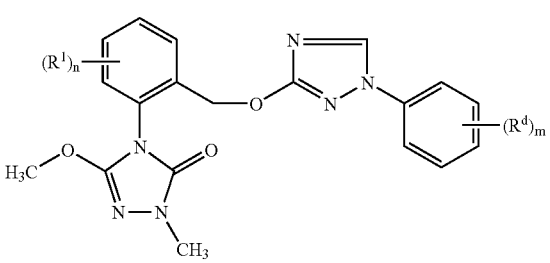

IB.7
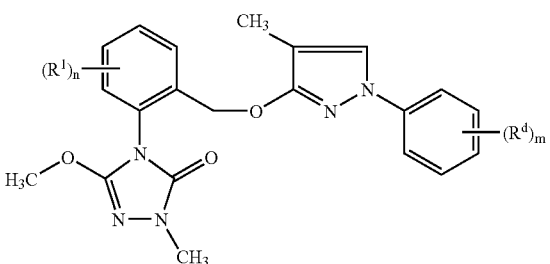

IB.8
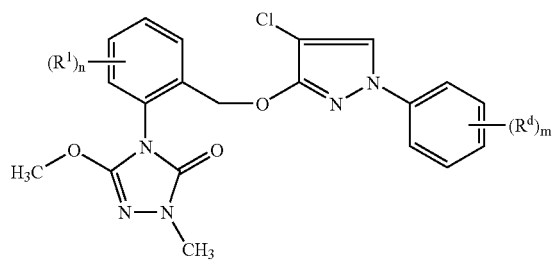

IB.9
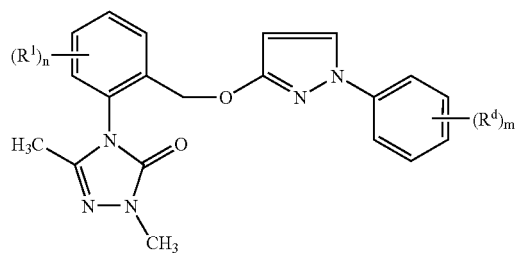

IB.10
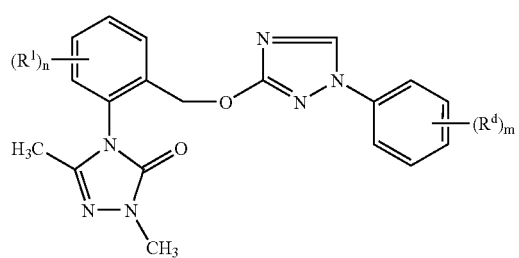

IB.11
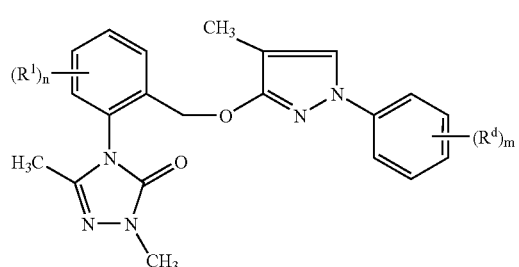

IB.12
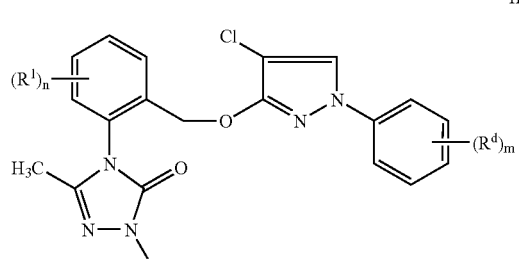

Equally, particular preference is given to compounds IC.1 and IC.2 in which $(R^1)_n$ is hydrogen, 6-chlororo or 6-methyl, $R^2$ is hydrogen or methyl and $R^3$ is cyclohexyl, benzyl, phenyl, pyridyl or pyrazinyl without substitution or with substitution by halogen or $C_1$–$C_4$-haloalkyl.

IC.1
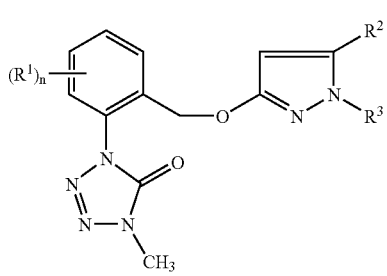

IC.2
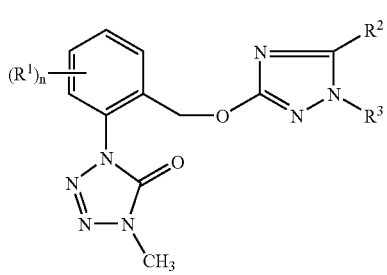

In addition, particular preference is given to compounds IC.3, IC.4, IC.5 and IC.6 in which $(R^1)_n$ is hydrogen, 6-chloro or 6-methyl, $R^d$ is halogen, nitro, cyano, $C_1$–$C_9$-alkyl, $C_1$–$C_2$-haloalkyl, cyclohexyl, $C_1$–$C_6$-alkoxy, $C_1$–$C_2$-haloalkoxy, phenyl-$C_1$–$C_3$-alkoxy or phenyl where the phenyl rings may be unsubstituted or substituted by halogen, methyl or methoxy, is pyridyl, $C_1$–$C_4$-alkoxycarbonyl, methoxymethyl or a group $C(CH_3)=N-C_1$–$C_4$-alkoxy and the index m is 1–5, in particular 1 or 2.

IC.3
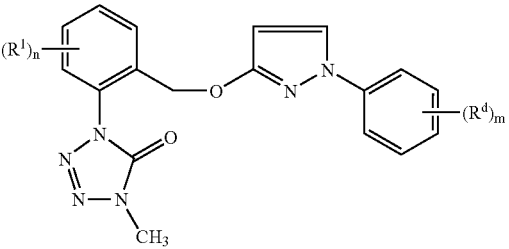

IC.4
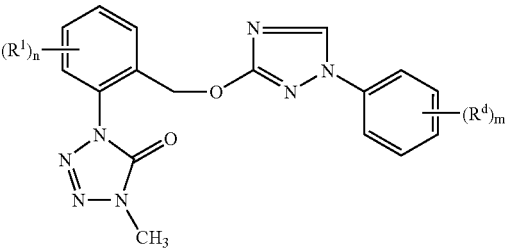

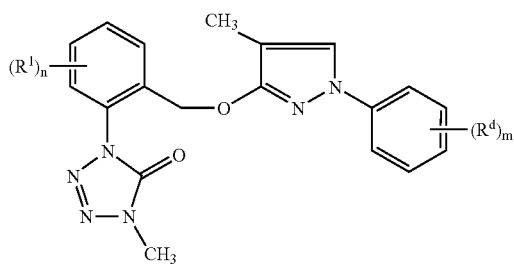

IC.5

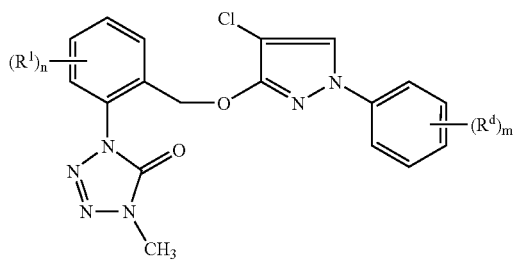

IC.6

With regard to the variables, the particularly preferred embodiments of the intermediates correspond to those of the groups and/or radicals A, B, C, Y, $R^a$, $R^b$, $(R^1)_n$, $R^2$ and $R^3$ of formula I.

With respect to their use, particular preference is given to the compounds I compiled in the tables below. Moreover, the groups mentioned for a substituent in the tables are, by themselves and independently of the combination in which they are mentioned, a particularly preferred embodiment of the substituent in question.

TABLE 1
Compounds of the formula IA.1 in which for each compound $(R^1)_n$, $R^2$ and $R^3$ correspond to one row of Table A

TABLE 2
Compounds of the formula IA.2 in which for each compound $R^{(1)}{}_n$, $R^2$ and $R^3$ correspond to one row of Table A

TABLE 3
Compounds of the formula IA.3 in which for each compound $(R^1)_n$, $R^2$ and $R^3$ correspond to one row of Table A

TABLE 4
Compounds of the formula IA.4 in which for each compound $(R^1)_n$, $R^3$ correspond to one row of Table A

TABLE 5
Compounds of the formula IA.5 in which $(R^1)_n$ is hydrogen and for each compound $(R^d)_m$ corresponds to one row of Table B

TABLE 6
Compounds of the formula IA.5 in which $(R^1)_n$ is 6-chlorine and for each compound $(R^d)_m$ corresponds to one row of Table B

TABLE 7
Compounds of the formula IA.5 in which $(R^1)_n$ is 6-methyl and for each compound $(R_d)_m$ corresponds to one row of Table B

TABLE 8
Compounds of the formula IA.6 in which $(R^1)_n$ is hydrogen and for each compound $(R^d)_m$ corresponds to one row of Table B

TABLE 9
Compounds of the formula IA.6 in which $(R^1)_n$ is 6-chlorine and for each compound $(R^d)_m$ corresponds to one row of Table B

TABLE 10
Compounds of the formula IA.6 in which $(R^1)_n$ is 6-methyl and for each compound $(R^d)_m$ corresponds to one row of Table B

TABLE 11
Compounds of the formula IA.7 in which $(R^1)_n$ is hydrogen and for each compound $(R^d)_m$ corresponds to one row of Table B

TABLE 12
Compounds of the formula IA.8 in which $(R^1)_n$ is hydrogen and for each compound $(R^d)_m$ corresponds to one row of Table B

TABLE 13
Compounds of the formula IA.9 in which $(R^1)_n$ is hydrogen and for each compound $(R^d)_m$ corresponds to one row of Table B

TABLE 14
Compounds of the formula IA.9 in which $(R^1)_n$ is 6-chlorine and for each compound $(R^d)_m$ corresponds to one row of Table B

TABLE 15
Compounds of the formula IA.9 in which $(R^1)_n$ is 6-methyl and for each compound $(R^d)_m$ corresponds to one row of Table B

TABLE 16
Compounds of the formula IA.10 in which $(R^1)_n$ is hydrogen and for each compound $(R^d)_m$ corresponds to one row of Table B

TABLE 17

Compounds of the formula IA.10 in which $(R^1)_n$ is 6-chlorine and for each compound $(R^d)_m$ corresponds to one row of Table B

TABLE 18

Compounds of the formula IA.10 in which $(R^1)_n$ is 6-methyl and for each compound $(R^d)_m$ corresponds to one row of Table B

TABLE 19

Compounds of the formula IA.11 in which $(R^1)_n$ is hydrogen and for each compound $(R^d)_m$ corresponds to one row of Table B

TABLE 20

Compounds of the formula IA.12 in which $(R^1)_n$ is hydrogen and for each compound $(R^d)_m$ corresponds to one row of Table B

TABLE 21

Compounds of the formula IB.1 in which for each compound $(R^1)_n$, $R^2$ and $R^3$ correspond to one row of Table A

TABLE 22

Compounds of the formula IB.2 in which for each compound $(R^1)_n$, $R^2$ and $R^3$ correspond to one row of Table A

TABLE 23

Compounds of the formula IB.3 in which for each compound $(R^1)_n$, $R^2$ and $R^3$ correspond to one row of Table A

TABLE 24

Compounds of the formula IB.4 in which for each compound $(R^1)_n$, $R^2$ and $R^3$ correspond to one row of Table A

TABLE 25

Compounds of the formula IB.5 in which $(R^1)_n$ is hydrogen and for each compound $(R^d)_m$ corresponds to one row of Table B

TABLE 26

Compounds of the formula IB.5 in which $(R^1)_n$ is 6-chloro and for each compound $(R^d)_m$ corresponds to one row of Table B

TABLE 27

Compounds of the formula IB.5 in which $(R^1)_n$ is 6-methyl and for each compound $(R^d)_m$ corresponds to one row of Table B

TABLE 28

Compounds of the formula IB.6 in which $(R^1)_n$ is hydrogen and for each compound $(R^d)_m$ corresponds to one row of Table B

TABLE 29

Compounds of the formula IB.6 in which $(R^1)_n$ is 6-chloro and for each compound $(R^d)_m$ corresponds to one row of Table B

TABLE 30

Compounds of the formula IB.6 in which $(R^1)_n$ is 6-methyl and for each compound $(R^d)_m$ corresponds to one row of Table B

TABLE 31

Compounds of the formula IB.7 in which $(R^1)_n$ is hydrogen and for each compound $(R^d)_m$ corresponds to one row of Table B

TABLE 32

Compounds of the formula IB.8 in which $(R^1)_n$ is hydrogen and for each compound $(R^d)_m$ corresponds to one row of Table B

TABLE 33

Compounds of the formula IB.9 in which $(R^1)_n$ is hydroqen and for each compound $(R^d)_m$ corresponds to one row of Table B

TABLE 34

Compounds of the formula IB.9 in which $(R^1)_n$ is 6-chloro and for each compound $(R^d)_m$ corresponds to one row of Table B

TABLE 35

Compounds of the formula IB.9 in which $(R^1)_n$ is 6-methyl and for each compound $(R^d)_m$ corresponds to one row of Table B

TABLE 36

Compounds of the formula IB.10 in which $(R^1)_n$ is hydrogen and for each compound $(R^d)_m$ corresponds to one row of Table B

TABLE 37

Compounds of the formula IB.10 in which $(R^1)_n$ is 6-chloro and for each compound $(R^d)_m$ corresponds to one row of Table B

TABLE 38

Compounds of the formula IB.10 in which $(R^1)_n$ is 6-methyl and for each compound $(R^d)_m$ corresponds to one row of Table B

TABLE 39

Compounds of the formula IB.11 in which $(R^1)_n$ is hydrogen and for each compound $(R^d)_m$ corresponds to one row of Table B

TABLE 40

Compounds of the formula IB.12 in which $(R^1)_n$ is hydrogen and for each compound $(R^d)_m$ corresponds to one row of Table B

TABLE 41

Compounds of the formula IC.1 in which for each compound $(R^1)_n$, $R^2$ and $R^3$ correspond to one row of Table A

TABLE 42

Compounds of the formula IC.2 in which for each compound $(R^1)_n$, $R^2$ and $R^3$ correspond to one row of Table A

TABLE 43

Compounds of the formula IC.3 in which $(R^1)_n$ is hydrogen and for each compound $(R^d)_m$ corresponds to one row of Table B

TABLE 44

Compounds of the formula IC.3 in which $(R^1)_n$ is 6-chloro and for each compound $(R^d)_m$ corresponds to one row of Table B

TABLE 45

Compounds of the formula IC.3 in which $(R^1)_n$ is 6-methyl and for each compound $(R^d)_m$ corresponds to one row of Table B

TABLE 46

Compounds of the formula IC.4 in which $(R^1)_n$ is hydrogen and for each compound $(R^d)_m$ corresponds to one row of Table B

TABLE 47

Compounds of the formula IC.4 in which $(R^1)_n$ is 6-chloro and for each compound $(R^d)_m$ corresponds to one row of Table B

TABLE 48

Compounds of the formula IC.4 in which $(R^1)_n$ is 6-methyl and for each compound $(R^d)_m$ corresponds to one row of Table B

TABLE 49

Compounds of the formula IC.5 in which $(R^1)_n$ is hydrogen and for each compound $(R^d)_m$ corresponds to one row of Table B

TABLE 50

Compounds of the formula IC.6 in which $(R^1)_n$ is hydrogen and for each compound $(R^d)_m$ corresponds to one row of Table B

TABLE A

| No. | $(R^1)_n$ | $R^2$ | $R^3$ |
|---|---|---|---|
| A-1 | H | H | cyclohexyl |
| A-2 | H | H | benzyl |
| A-3 | H | H | phenyl |
| A-4 | H | H | 2-pyridyl |
| A-5 | H | H | 5-Cl-pyridyl-2 |
| A-6 | H | H | 5-$CF_3$-pyridyl-2 |
| A-7 | H | H | 2-pyrazinyl |
| A-8 | H | $CH_3$ | cyclohexyl |
| A-9 | H | $CH_3$ | benzyl |
| A-10 | H | $CH_3$ | phenyl |
| A-11 | H | $CH_3$ | 2-pyridyl |
| A-12 | H | $CH_3$ | 5-Cl-pyridyl-2 |
| A-13 | H | $CH_3$ | 5-$CF_3$-pyridyl-2 |
| A-14 | H | $CH_3$ | 2-pyrazinyl |
| A-15 | 6-Cl | H | cyclohexyl |
| A-16 | 6-Cl | H | benzyl |
| A-17 | 6-Cl | H | phenyl |
| A-18 | 6-Cl | H | 2-pyridyl |
| A-19 | 6-Cl | H | 5-Cl-pyridyl-2 |
| A-20 | 6-Cl | H | 5-$CF_3$-pyridyl-2 |
| A-21 | 6-Cl | H | 2-pyrazinyl |
| A-22 | 6-Cl | $CH_3$ | cyclohexyl |
| A-23 | 6-Cl | $CH_3$ | benzyl |
| A-24 | 6-Cl | $CH_3$ | phenyl |
| A-25 | 6-Cl | $CH_3$ | 2-pyridyl |
| A-26 | 6-Cl | $CH_3$ | 5-Cl-pyridyl-2 |
| A-27 | 6-Cl | $CH_3$ | 5-$CF_3$-pyridyl-2 |
| A-28 | 6-Cl | $CH_3$ | 2-pyrazinyl |
| A-29 | 6-$CH_3$ | H | cyclohexyl |
| A-30 | 6-$CH_3$ | H | benzyl |
| A-31 | 6-$CH_3$ | H | phenyl |
| A-32 | 6-$CH_3$ | H | 2-pyridyl |
| A-33 | 6-$CH_3$ | H | 5-Cl-pyridyl-2 |
| A-34 | 6-$CH_3$ | H | 5-$CF_3$-pyridyl-2 |
| A-35 | 6-$CH_3$ | H | 2-pyrazinyl |
| A-36 | 6-$CH_3$ | $CH_3$ | cyclohexyl |
| A-37 | 6-$CH_3$ | $CH_3$ | benzyl |
| A-38 | 6-$CH_3$ | $CH_3$ | phenyl |
| A-39 | 6-$CH_3$ | $CH_3$ | 2-pyridyl |
| A-40 | 6-$CH_3$ | $CH_3$ | 5-Cl-pyridyl-2 |
| A-41 | 6-$CH_3$ | $CH_3$ | 5-$CF_3$-pyridyl-2 |
| A-42 | 6-$CH_3$ | $CH_3$ | 2-pyrazinyl |

TABLE B

| No. | $(R^d)_m$ |
|---|---|
| B-1 | H |
| B-2 | 2-F |
| B-3 | 3-F |
| B-4 | 4-F |
| B-5 | 2,4-$F_2$ |
| B-6 | 2,4,6-$F_3$ |
| B-7 | 2,3,4,5,6-$F_5$ |
| B-8 | 2,3-$F_2$ |
| B-9 | 2-Cl |
| B-10 | 3-Cl |
| B-11 | 4-Cl |
| B-12 | 2,3-$Cl_2$ |
| B-13 | 2,4-$Cl_2$ |
| B-14 | 2,5-$Cl_2$ |
| B-15 | 2,6-$Cl_2$ |
| B-16 | 3,4-$Cl_2$ |
| B-17 | 3,5-$Cl_2$ |
| B-18 | 2,3,4-$Cl_3$ |
| B-19 | 2,3,5-$Cl_3$ |
| B-20 | 2,3,6-$Cl_3$ |

TABLE B-continued

| No. | $(R^d)_m$ |
|---|---|
| B-21 | 2,4,5-Cl$_3$ |
| B-22 | 2,4,6-Cl$_3$ |
| B-23 | 3,4,5-Cl$_3$ |
| B-24 | 2,3,4,6-Cl$_4$ |
| B-25 | 2,3,5,6-Cl$_4$ |
| B-26 | 2,3,4,5,6-Cl$_5$ |
| B-27 | 2-Br |
| B-28 | 3-Br |
| B-29 | 4-Br |
| B-30 | 2,4-Br$_2$ |
| B-31 | 2,5-Br$_2$ |
| B-32 | 2,6-Br$_2$ |
| B-33 | 2,4,6-Br$_3$ |
| B-34 | 2,3,4,5,6-Br$_5$ |
| B-35 | 2-J |
| B-36 | 3-J |
| B-37 | 4-J |
| B-38 | 2,4-J$_2$ |
| B-39 | 2-Cl, 3-F |
| B-40 | 2-Cl, 4-F |
| B-41 | 2-Cl, 5-F |
| B-42 | 2-Cl, 6-F |
| B-43 | 2-Cl, 3-Br |
| B-44 | 2-Cl, 4-Br |
| B-45 | 2-Cl, 5-Br |
| B-46 | 2-Cl, 6-Br |
| B-47 | 2-Br, 3-Cl |
| B-48 | 2-Br, 4-Cl |
| B-49 | 2-Br, 5-Cl |
| B-50 | 2-Br, 3-F |
| B-51 | 2-Br, 4-F |
| B-52 | 2-Br, 5-F |
| B-53 | 2-Br, 6-F |
| B-54 | 2-F, 3-Cl |
| B-55 | 2-F, 4-Cl |
| B-56 | 2-F, 5-Cl |
| B-57 | 3-Cl, 4-F |
| B-58 | 3-Cl, 5-F |
| B-59 | 3-Cl, 4-Br |
| B-60 | 3-Cl, 5-Br |
| B-61 | 3-F, 4-Cl |
| B-62 | 3-F, 4-Br |
| B-63 | 3-Br, 4-Cl |
| B-64 | 3-Br, 4-F |
| B-65 | 2,6-Cl$_2$, 4-Br |
| B-66 | 2-CH$_3$ |
| B-67 | 3-CH$_3$ |
| B-68 | 4-CH$_3$ |
| B-69 | 2,3-(CH$_3$)$_2$ |
| B-70 | 2,4-(CH$_3$)$_2$ |
| B-71 | 2,5-(CH$_3$)$_2$ |
| B-72 | 2,6-(CH$_3$)$_2$ |
| B-73 | 3,4-(CH$_3$)$_2$ |
| B-74 | 3,5-(CH$_3$)$_2$ |
| B-75 | 2,3,5-(CH$_3$)$_3$ |
| B-76 | 2,3,4-(CH$_3$)$_3$ |
| B-77 | 2,3,6-(CH$_3$)$_3$ |
| B-78 | 2,4,5-(CH$_3$)$_3$ |
| B-79 | 2,4,6-(CH$_3$)$_3$ |
| B-80 | 3,4,5-(CH$_3$)$_3$ |
| B-81 | 2,3,4,6-(CH$_3$)$_4$ |
| B-82 | 2,3,5,6-(CH$_3$)$_4$ |
| B-83 | 2,3,4,5,6-(CH$_3$)$_5$ |
| B-84 | 2-C$_2$H$_5$ |
| B-85 | 3-C$_2$H$_5$ |
| B-86 | 4-C$_2$H$_5$ |
| B-87 | 2,4-(C$_2$H$_5$)$_2$ |
| B-88 | 2,6-(C$_2$H$_5$)$_2$ |
| B-89 | 3,5-(C$_2$H$_5$)$_2$ |
| B-90 | 2,4,6-(C$_2$H$_5$)$_3$ |
| B-91 | 2-n-C$_3$H$_7$ |
| B-92 | 3-n-C$_3$H$_7$ |
| B-93 | 4-n-C$_3$H$_7$ |
| B-94 | 2-i-C$_3$H$_7$ |
| B-95 | 3-i-C$_3$H$_7$ |
| B-96 | 4-i-C$_3$H$_7$ |
| B-97 | 2,4-(i-C$_3$H$_7$)$_2$ |
| B-98 | 2,6-(i-C$_3$H$_7$)$_2$ |
| B-99 | 3,5-(i-C$_3$H$_7$)$_2$ |
| B-100 | 2-s-C$_4$H$_9$ |
| B-101 | 3-s-C$_4$H$_9$ |
| B-102 | 4-s-C$_4$H$_9$ |
| B-103 | 2-t-C$_4$H$_9$ |
| B-104 | 3-t-C$_4$H$_9$ |
| B-105 | 4-t-C$_4$H$_9$ |
| B-106 | 4-n-C$_9$H$_{19}$ |
| B-107 | 2-CH$_3$, 4-t-C$_4$H$_9$ |
| B-108 | 2-CH$_3$, 6-t-C$_4$H$_9$ |
| B-109 | 2-CH$_3$, 4-i-C$_3$H$_7$ |
| B-110 | 2-CH$_3$, 5-i-C$_3$H$_7$ |
| B-111 | 3-CH$_3$, 4-i-C$_3$H$_7$ |
| B-112 | 2-cyclo-C$_6$H$_{11}$ |
| B-113 | 3-cyclo-C$_6$H$_{11}$ |
| B-114 | 4-cyclo-C$_6$H$_{11}$ |
| B-115 | 2-Cl, 4-C$_6$H$_5$ |
| B-116 | 2-Br, 4-C$_6$H$_5$ |
| B-117 | 2-OCH$_3$ |
| B-118 | 3-OCH$_3$ |
| B-119 | 4-OCH$_3$ |
| B-120 | 2-OC$_2$H$_5$ |
| B-121 | 3-O-C$_2$H$_5$ |
| B-122 | 4-O-C$_2$H$_5$ |
| B-123 | 2-O-n-C$_3$H$_7$ |
| B-124 | 3-O-n-C$_3$H$_7$ |
| B-125 | 4-O-n-C$_3$H$_7$ |
| B-126 | 2-O-i-C$_3$H$_7$ |
| B-127 | 3-O-i-C$_3$H$_7$ |
| B-128 | 4-O-i-C$_3$H$_7$ |
| B-129 | 2-O-n-C$_6$H$_{13}$ |
| B-130 | 3-O-n-C$_6$H$_{13}$ |
| B-131 | 4-O-n-C$_6$H$_{13}$ |
| B-132 | 2-O-CH$_2$C$_6$H$_5$ |
| B-133 | 3-O-CH$_2$C$_6$H$_5$ |
| B-134 | 4-O-CH$_2$C$_6$H$_5$ |
| B-135 | 2-O-(CH$_2$)$_3$C$_6$H$_5$ |
| B-136 | 4-O-(CH$_2$)$_3$C$_6$H$_5$ |
| B-137 | 2,3-(OCH$_3$)$_2$ |
| B-138 | 2,4-(OCH$_3$)$_2$ |
| B-139 | 2,5-(OCH$_3$)$_2$ |
| B-140 | 2,6-(OCH$_3$)$_2$ |
| B-141 | 3,4-(OCH$_3$)$_2$ |
| B-142 | 3,5-(OCH$_3$)$_2$ |
| B-143 | 2-O-t-C$_4$H$_9$ |
| B-144 | 3-O-t-C$_4$H$_9$ |
| B-145 | 4-O-t-C$_4$H$_9$ |
| B-146 | 3-(3'-Cl—C$_6$H$_4$) |
| B-147 | 4-(4'-CH$_3$—C$_6$H$_4$) |
| B-148 | 2-O-C$_6$H$_5$ |
| B-149 | 3-O-C$_6$H$_5$ |
| B-150 | 4-O-C$_6$H$_5$ |
| B-151 | 2-O-(2'-F—C$_6$H$_4$) |
| B-152 | 3-O-(3'-Cl—C$_6$H$_4$) |
| B-153 | 4-O-(4'-CH$_3$—C$_6$H$_4$) |
| B-154 | 2,3,6-(CH$_3$)$_3$, 4-F |
| B-155 | 2,3,6-(CH$_3$)$_3$, 4-Cl |
| B-156 | 2,3,6-(CH$_3$)$_3$, 4-Br |
| B-157 | 2,4-(CH$_3$)$_2$, 6-F |
| B-158 | 2,4-(CH$_3$)$_2$, 6-Cl |
| B-159 | 2,4-(Ch$_3$)$_2$, 6-Br |
| B-160 | 2-i-C$_3$H$_7$, 4-Cl, 5-CH$_3$ |
| B-161 | 2-Cl, 4-NO$_2$ |
| B-162 | 2-NO$_2$, 4-Cl |
| B-163 | 2-OCH$_3$, 5-NO$_2$ |
| B-164 | 2,4-Cl$_2$, 5-NO$_2$ |
| B-165 | 2,4-Cl$_2$, 6-NO$_2$ |
| B-166 | 2,6-Cl$_2$, 4-NO$_2$ |
| B-167 | 2,6-Br$_2$, 4-NO$_2$ |
| B-168 | 2,6-J$_2$, 4-NO$_2$ |
| B-169 | 2-CH$_3$, 5-i-C$_3$H$_7$, 4-Cl |
| B-170 | 2-CO$_2$CH$_3$ |
| B-171 | 3-CO$_2$CH$_3$ |
| B-172 | 4-CO$_2$CH$_3$ |
| B-173 | 2-CH$_2$—OCH$_3$ |
| B-174 | 3-CH$_2$—OCH$_3$ |

TABLE B-continued

| No. | $(R^d)_m$ |
|---|---|
| B-175 | 4-CH$_2$—OCH$_3$ |
| B-176 | 2-Me-4-CH$_3$—CH(CH$_3$)—CO |
| B-177 | 2-CH$_3$-4-(CH$_3$—C=NOCH$_3$) |
| B-178 | 2-CH$_3$-4-(CH$_3$—C=NOC$_2$H$_5$) |
| B-179 | 2-CH$_3$-4-(CH$_3$—C=NO-n-C$_3$H$_7$) |
| B-180 | 2-CH$_3$-4-(CH$_3$—C=NO-i-C$_3$H$_7$) |
| B-181 | 2,5-(CH$_3$)$_2$-4-(CH$_3$—C=NOCH$_3$) |
| B-182 | 2,5-(CH$_3$)$_2$-4-(CH$_3$—C=NOC$_2$H$_5$) |
| B-183 | 2,5-(CH$_3$-4-(CH$_3$—C=NO-n-C$_3$H$_7$) [sic] |
| B-184 | 2,5-(CH$_3$)$_2$-4-(CH$_3$—C=NO-i-C$_3$H$_7$) |
| B-185 | 2-C$_6$H$_5$ |
| B-186 | 3-C$_6$H$_5$ |
| B-187 | 4-C$_6$H$_5$ |
| B-188 | 2-(2'-F—C$_6$H$_4$) |
| B-189 | 2-CH$_3$, 5-Br |
| B-190 | 2-CH$_3$, 6-Br |
| B-191 | 2-Cl, 3-CH$_3$ |
| B-192 | 2-Cl, 4-CH$_3$ |
| B-193 | 2-Cl, 5-CH$_3$ |
| B-194 | 2-F, 3-CH$_3$ |
| B-195 | 2-F, 4-CH$_3$ |
| B-196 | 2-F, 5-CH$_3$ |
| B-197 | 2-Br, 3-CH$_3$ |
| B-198 | 2-Br, 4-CH$_3$ |
| B-199 | 2-Br, 5-CH$_3$ |
| B-200 | 3-CH$_3$, 4-Cl |
| B-201 | 3-Ch$_3$, 5-Cl |
| B-202 | 3-Ch$_3$, 4-F |
| B-203 | 3-Ch$_3$, 5-F |
| B-204 | 3-Ch$_3$, 4-Br |
| B-205 | 3-Ch$_3$, 5-Br |
| B-206 | 3-F, 4-CH$_3$ |
| B-207 | 3-Cl, 4-CH$_3$ |
| B-208 | 3-Br, 4-CH$_3$ |
| B-209 | 2-Cl,4, 5-(CH$_3$)$_2$ |
| B-210 | 2-Br,4, 5-(CH$_3$)$_2$ |
| B-211 | 2-Cl,3, 5-(CH$_3$)$_2$ |
| B-212 | 2-Br,3, 5-CH$_3$)$_2$ |
| B-213 | 2,6-Cl$_2$, 4-CH$_3$ |
| B-214 | 2,6-F$_2$, 4-CH$_3$ |
| B-215 | 2,6-Br$_2$, 4-CH$_3$ |
| B-216 | 2,4-Br$_2$, 6-CH$_3$ |
| B-217 | 2,4-F$_2$, 6-CH$_3$ |
| B-218 | 2,4-Br$_2$, 6-CH$_3$ |
| B-219 | 2,6-(CH$_3$)$_2$, 4-F |
| B-220 | 2,6-(CH$_3$)$_2$, 4-Cl |
| B-221 | 2,6-(CH$_3$)$_2$, 4-Br |
| B-222 | 3,5-(CH$_3$)$_2$, 4-F |
| B-223 | 3,5-(CH$_3$)$_2$, 4-Cl |
| B-224 | 3,5-(CH$_3$)$_2$, 4-Br |
| B-225 | 2-CF$_3$ |
| B-226 | 3-CF$_3$ |
| B-227 | 4-CF$_3$ |
| B-228 | 2-OCF$_3$ |
| B-229 | 3-OCF$_3$ |
| B-230 | 4-OCF$_3$ |
| B-231 | 3-OCH$_2$CHF$_2$ |
| B-232 | 2-NO$_2$ |
| B-233 | 3-NO$_2$ |
| B-234 | 4-NO$_2$ |
| B-235 | 2-CN |
| B-236 | 3-CN |
| B-237 | 4-CN |
| B-238 | 2-CH$_3$, 3-Cl |
| B-239 | 2-CH$_3$, 4-Cl |
| B-240 | 2-CH$_3$, 5-Cl |
| B-241 | 2-CH$_3$, 6-Cl |
| B-242 | 2-CH$_3$, 3-F |
| B-243 | 2-CH$_3$, 4-F |
| B-244 | 2-CH$_3$, 5-F |
| B-245 | 2-CH$_3$, 6-F |
| B-246 | 2-CH$_3$, 3-Br |
| B-247 | 2-CH$_3$, 4-Br |
| B-248 | 2-pyridyl-2' |
| B-249 | 3-pyridyl-3' |
| B-250 | 4-pyridyl-4' |

The compounds I are suitable as fungicides. They have excellent activity against a broad spectrum of phytopathogenic fungi, in particular from the class of the Ascomycetes, Deuteromycetes, Phycomycetes and Basidiomycetes. Some of them act systemically and can be employed in crop protection as foliar- and soil-acting fungicides.

They are especially important for controlling a large number of fungi in a variety of crop plants such as wheat, rye, barley, oats, rice, maize, grass, bananas, cotton, soy, coffee, sugar cane, grapevines, fruit species, ornamentals and vegetable species such as cucumbers, beans, tomatoes, potatoes and curcubits, and also in the seeds of these plants.

Specifically, they are suitable for controlling the following plant diseases:

Alternaria species in vegetables and fruit,
Botrytis cinerea (gray mold) in strawberries, vegetables, ornamentals and grapevines,
Cercospora arachidicola in groundnuts,
Erysiphe cichoracearum and Sphaerotheca fuliginea in curcubits,
Erysiphe graminis (powdery mildew) in cereals,
Fusarium and Verticillium species in a variety of plants,
Helminthosporium species in cereals,
Mycosphaerella species in bananas and groundnuts,
Phytophthora infestans in potatoes and tomatoes,
Plasmopara viticola in grapevines,
Podosphaera leucotricha in apples,
Pseudocercosporella herpotrichoides in wheat and barley,
Pseudoperonospora species in hops and cucumbers,
Puccinia species in cereals,
Pyricularia oryzae in rice,
Rhizoctonia species in cotton, rice and lawn,
Septoria nodorum in wheat,
Uncinula necator in grapevines,
Ustilago species in cereals and sugar cane, and
Venturia species (scab) in apples and pears.

In addition, the compounds I are suitable for controlling harmful fungi such as *Paecilomyces variotii* in the protection of materials (for example wood, paper, paint dispersions, fibers or tissues) and in the protection of stored products.

The compounds I are employed by treating the fungi or the plants, seeds, materials or the soil to be protected from being attacked by fungi with a fungicidally effective amount of the active compounds. The application may be carried out before or after the infection of the materials, plants or seeds by the fungi.

The fungicidal compositions generally comprise from 0.1 to 95, preferably from 0.5 to 90, % by weight of active compound.

For use in crop protection, the application rates are, depending in each case on the kind of desired effect, from 0.01 to 2.0 kg of active compound per ha.

The treatment of seeds generally requires active compound quantities from 0.001 to 0.1 g, preferably from 0.01 to 0.05 g, per kilogram of seeds.

For use in the protection of materials or stored products, the active compound application rate depends on the kind of application area and desired effect. Customary application rates in the protection of materials are, for example, from 0.001 g to 2 kg, preferably from 0.005 g to 1 kg, of active compound per cubic meter of treated material.

The compounds of the formula I are also suitable for the efficient control of animal pests from the class of insects, arachnids and nematodes. They can be used in crop protection and in the hygiene sector, in the protection of materials and the veterinary sector for controlling animal pests. They are particularly suitable for controlling the following animal pests:

insects from the order of the lepidopterans (Lepidoptera), for example *Agrotis ypsilon, Agrotis segetum, Alabama argillacea, Anticarsia gemmatalis, Argyresthia conjugella, Autographa gamma, Bupalus piniarius, Cacoecia murinana, Capua reticulana, Cheimatobia brumata, Choristoneura fumiferana, Choristoneura occidentalis, Cirphis unipuncta, Cydia pomonella, Dendrolimus pini, Diaphania nitidalis, Diatraea grandiosella, Earias insulana, Elasmopalpus lignosellus, Eupoecilia ambiguella, Evetria bouliana, Feltia subterranea, Galleria mellonella, Grapholitha funebrana, Grapholitha molesta, Heliothis armigera, Heliothis virescens, Heliothis zea, Hellula undalis, Hibernia defoliaria, Hyphantria cunea, Hyponomeuta malinellus, Keiferia lycopersicella, Lambdina fiscellaria, Laphygma exigua, Leucoptera coffeella, Leucoptera scitella, Lithocolletis blancardella, Lobesia botrana, Loxostege sticticalis, Lymantria dispar, Lymantria monacha, Lyonetia clerkella, Malacosoma neustria, Mamestra brassicae, Orgyia pseudotsugata, Ostrinia nubilalis, Panolis flammea, Pectinophora gossypiella, Peridroma saucia, Phalera bucephala, Phthorimaea operculella, Phyllocnistis citrella, Pieris brassicae, Plathypena scabra, Plutella xylostella, Pseudoplusia includens, Rhyacionia frustrana, Scrobipalpula absoluta, Sitotroga cerealella, Sparganothis pilleriana, Spodoptera frugiperda, Spodoptera littoralis, Spodoptera litura, Thaumatopoea pityocampa, Tortrix viridana, Trichoplusia ni* and *Zeiraphera canadensis,* beetles (Coleoptera), for example *Agrilus sinuatus, Agriotes lineatus, Agriotes obscurus, Amphimallus solstitialis, Anisandrus dispar, Anthonomus grandis, Anthonomus pomorum, Atomaria linearis, Blastophagus piniperda, Blitophaga undata, Bruchus rufimanus, Bruchus pisorum, Bruchus lentis, Byctiscus betulae, Cassida nebulosa, Cerotoma trifurcata, Ceuthorrhynchus assimilis, Ceuthorrhynchus napi, Chaetocnema tibialis, Conoderus vespertinus, Crioceris asparagi, Diabrotica longicornis, Diabrotica 12-punctata, Diabrotica virgifera, Epilachna varivestis, Epitrix hirtipennis, Eutinobothrus brasiliensis, Hylobius abietis, Hypera brunneipennis, Hypera postica, Ips typographus, Lema bilineata, Lema melanopus, Leptinotarsa decemlineata, Limonius californicus, Lissorhoptrus oryzophilus, Melanotus communis, Meligethes aeneus, Melolontha hippocastani, Melolontha melolontha, Oulema oryzae, Ortiorrhynchus sulcatus, Otiorrhynchus ovatus, Phaedon cochleariae, Phyllotreta chrysocephala,* Phyllophaga sp., *Phyllopertha horticola, Phyllotreta nemorum, Phyllotreta striolata, Popillia japonica, Sitona lineatus* and *Sitophilus granaria,* dipterans (Diptera), for example *Aedes aegypti, Aedes vexans, Anastrepha ludens, Anopheles maculipennis, Ceratitis capitata, Chrysomya bezziana, Chrysomya hominivorax, Chrysomya macellaria, Contarinia sorghicola, Cordylobia anthropophaga, Culex pipiens, Dacus cucurbitae, Dacus oleae, Dasineura brassicae, Fannia canicularis, Gasterophilus intestinalis, Glossina morsitans, Haematobia irritans, Haplodiplosis equestris, Hylemyia platura, Hypoderma lineata, Liriomyza sativae, Liriomyza trifolii, Lucilia caprina, Lucilia cuprina, Lucilia sericata, Lycoria pectoralis, Mayetiola destructor, Musca domestica, Muscina stabulans, Oestrus ovis, Oscinella frit, Pegomya hysocyami, Phorbia antiqua, Phorbia brassicae, Phorbia coarctata, Rhagoletis cerasi, Rhagoletis pomonella, Tabanus bovinus, Tipula oleracea*and *Tipula paludosa,* thrips (Thysanoptera), for example *Frankliniella fusca, Frankliniella occidentalis, Frankliniella tritici, Scirtothrips citri, Thrips oryzae, Thrips palmi* and *Thrips tabaci,* hymenopterans (Hymenoptera), for example *Athalia rosae, Atta cephalotes, Atta sexdens, Atta texana, Hoplocampa minuta, Hoplocampa testudinea, Monomorium pharaonis, Solenopsis geminata* and *Solenopsis invicta,* heteropterans (Heteroptera), for example *Acrosternum hilare, Blissus leucopterus, Cyrtopeltis notatus, Dysdercus cingulatus, Dysdercus intermedius, Eurygaster integriceps, Euschistus impictiventris, Leptoglossus phyllopus, Lygus lineolaris, Lygus pratensis, Nezara viridula, Piesma quadrata, Solubea insularis* and *Thyanta perditor,* homopterans (Homoptera), for example *Acyrthosiphon onobrychis, Adelges laricis, Aphidula nasturtii, Aphis fabae, Aphis pomi, Aphis sambuci, Brachycaudus cardui, Brevicoryne brassicae, Cerosipha gossypii, Dreyfusia nordmannianae, Dreyfusia piceae, Dysaphis radicola, Dysaulacorthum pseudosolani, Empoasca fabae, Macrosiphum avenae, Macrosiphum euphorbiae, Macrosiphon rosae, Megoura viciae, Metopolophium dirhodum, Myzodes persicae, Myzus cerasi, Nilaparvata lugens, Pemphigus bursarius, Perkinsiella saccharicida, Phorodon humuli, Psylla mali, Psylla piri, Rhopalomyzus ascalonicus, Rhopalosiphum maidis, Sappaphis mala, Sappaphis mali, Schizaphis graminum, Schizoneura lanuginosa, Trialeurodes vaporariorum* and *Viteus vitifolii,* termites (Isoptera), for example *Calotermes flavicollis, Leucotermes flavipes, Reticulitermes lucifugus* and *Termes natalensis,* orthopterans (Orthoptera), for example *Acheta domestica, Blatta orientalis, Blattella germanica, Forficula auricularia, Gryllotalpa gryllotalpa, Locusta migratoria, Melanoplus bivittatus, Melanoplus femurrubrum, Melanoplus mexicanus, Melanoplus sanguinipes, Melanoplus spretus, Nomadacris septemfasciata, Periplaneta americana, Schistocerca americana, Schistocerca peregrina, Stauronotus maroccanus* and *Tachycines asynamorus,* arachnoidea such as arachnids (Acarina), for example *Amblyomma americanum, Amblyomma variegatum, Argas persicus, Boophilus annulatus, Boophilus decoloratus, Boophilus microplus, Brevipalpus phoenicis, Bryobia praetiosa, Dermacentor silvarum, Eotetranychus carpini, Eriophyes sheldoni, Hyalomma truncatum, Ixodes ricinus, Ixodes rubicundus, Ornithodorus moubata, Otobius megnini, Paratetranychus pilosus, Dermanyssus gallinae, Phyllocoptruta oleivora, Polyphagotarsonemus latus, Psoroptes ovis, Rhipicephalus appendiculatus, Rhipicephalus evertsi, Sarcoptes scabiei, Tetranychus cinnabarinus, Tetranychus kanzawai, Tetranychus pacificus, Tetranychus telarius* and *Tetranychus urticae,* nematodes such as root gall nematodes, for example *Meloidogyne hapla, Meloidogyne incognita, Meloidogyne javanica,* cyst-forming nematodes, for example

*Globodera rostochiensis, Heterodera avenae, Heterodera glycines, Heterodera schachtii, Heterodera trifolii*, stem and leaf nematodes, for example *Belonolaimus longicaudatus, Ditylenchus destructor, Ditylenchus dipsaci, Heliocotylenchus multicinctus, Longidorus elongatus, Radopholus similis, Rotylenchus robustus, Trichodorus primitivus, Tylenchorhynchus claytoni, Tylenchorhynchus dubius, Pratylenchus neglectus, Pratylenchus penetrans, Pratylenchus curvitatus* and *Pratylenchus goodeyi*.

For controlling animal pests under free-range conditions, the application rate of active compound is from 0.1 to 2.0, preferably from 0.2 to 1.0, kg/ha.

The compounds I can be converted into the customary formulations, for example solutions, emulsions, suspensions, dusts, powders, pastes and granules. The application form depends on the particular intended use; in each case it should guarantee a fine and even distribution of the compound according to the invention.

The formulations are prepared in a known manner, for example by extending the active compound with solvents and/or carriers, if desired using emulsifiers and dispersants, where, if water is used as a diluent, other organic solvents can also be used as auxiliary solvents. Suitable auxiliaries for this purpose are essentially: solvents such as aromatics (for example xylene), chlorinated aromatics (for example chlorobenzenes), paraffins (for example petroleum fractions), alcohols (for example methanol, butanol), ketones (for example cyclohexanone), amines (for example ethanolamine, dimethylformamide) and water; carriers such as ground natural minerals (for example kaolins, argillaceous earths, talc, chalk) and ground synthetic minerals (for example finely divided silica, silicates); emulsifiers such as nonionic and anionic emulsifiers (for example polyoxyethylene fatty alcohol ethers, alkylsulfonates and arylsulfonates) and dispersants such as lignosulfite waste liquors and methylcellulose.

Suitable surfactants are the alkali metal, alkaline earth metal and ammonium salts of lignosulfonic acid, naphthalenesulfonic acid, phenolsulfonic acid, dibutylnaphthalenesulfonic acid, alkylarylsulfonates, alkyl sulfates, alkylsulfonates, fatty alcohol sulfates and fatty acids and alkali metal salts-and alkaline earth metal salts thereof, salts of sulfated fatty alcohol glycol ethers, condensation products of sulfonated naphthalene and naphthalene derivatives with formaldehyde, condensation products of naphthalene or of naphthalenesulfonic acid with phenol and formaldehyde, polyoxyethylene octylphenol ethers, ethoxylated isooctylphenol, octylphenol and nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignosulfite waste liquors and methylcellulose.

Suitable for preparing directly sprayable solutions, emulsions, pastes or oil dispersions are petroleum fractions having medium to high boiling points, such as kerosene or diesel fuel, furthermore coal-tar oils and oils of plant or animal origin, aliphatic, cyclic and aromatic hydrocarbons, for example benzene, toluene, xylene, paraffin, tetrahydronaphthalene, alkylated naphthalenes or derivatives thereof, methanol, ethanol, propanol, butanol, chloroform, carbon tetrachloride, cyclohexanol, cyclohexanone, chlorobenzene, isophorone, strongly polar solvents, for example dimethylformamide, dimethyl sulfoxide, N-methylpyrrolidone and water.

Powders, compositions for broadcasting and dusts can be prepared by mixing or joint grinding of the active substances with a solid carrier.

Granules, for example coated granulates, impregnated granules and homogenous granules, can be prepared by binding the active ingredients to solid carriers. Solid carriers are, for example, mineral earths, such as silica gel, silicas, silica gels, silicates, talc, kaolin, attaclay, limestone, lime, chalk, bole, loess, clay, dolomite, diatomaceous earth, calcium sulfate, magnesium sulfate, magnesium oxide, ground synthetic materials, fertilizers, such as ammonium sulfate, ammonium phosphate, ammonium nitrate, ureas and products of plant origin, such as cereal meal, tree bark meal, wood meal and nutshell meal, cellulose powders and other solid carriers.

The formulations generally comprise from 0.01 to 95% by weight, preferably from 0.1 to 90% by weight, of the active compound. The active compounds are employed in a purity of from 90% to 100%, preferably from 95% to 100% (according to NMR spectrum).

Examples of Formulations are:

I. 5 parts by weight of a compound according to the invention are thoroughly mixed with 95 parts by weight of finely divided kaolin. This affords a dusting composition comprising 5% by weight of the active compound.

II. 30 parts by weight of a compound according to the invention are thoroughly mixed with a mixture of 92 parts by weight of pulverulent silica gel and 8 parts by weight of paraffin oil which had been sprayed onto the surface of this silica gel. This affords an active compound preparation having good adhesive properties (active compound content 23% by weight).

III. 10 parts by weight of a compound according to the invention are dissolved in a mixture comprising 90 parts by weight of xylene, 6 parts by weight of the addition product of 8 to 10 mol of ethylene oxide to 1 mol of oleic acid N-monoethanolamide, 2 parts by weight of the calcium salt of dodecylbenzenesulfonic acid and 2 parts by weight of the addition product of 40 mol of ethylene oxide to 1 mol of castor oil (active compound content 9% by weight).

IV. 20 parts by weight of a compound according to the invention are dissolved in a mixture comprising 60 parts by weight of cyclohexanone, 30 parts by weight of isobutanol, 5 parts by weight of the addition product of 7 mol of ethylene oxide to 1 mol of isooctylphenol and 5 parts by weight of the addition product of 40 mol of ethylene oxide to 1 mol of castor oil (active compound content 16% by weight).

V. 80 parts by weight of a compound according to the invention are mixed well with 3 parts by weight of the sodium salt of diisobutylnaphthalene-alpha-sulfonic acid, 10 parts by weight of the sodium salt of a lignosulfonic acid from a sulfite waste liquor and 7 parts by weight of pulverulent silica gel, and ground in a hammer mill (active compound content 80% by weight).

VI. 90 parts by weight of a compound according to the invention are mixed with 10 parts by weight of N-methyl-α-pyrrolidone, affording a solution which is suitable for use in the form of very small drops (active compound content 90% by weight).

VII. 20 parts by weight of a compound according to the invention are dissolved in a mixture comprising 40 parts by weight of cyclohexanone, 30 parts by weight of isobutanol, 20 parts by weight of the addition product of 7 mol of ethylene oxide to 1 mol of isooctylphenol and 10 parts by weight of the addition product of 40 mol of ethylene oxide to 1 mol of castor oil. The solution is poured into 100,000 parts by weight of water and finely dispersed therein, affording an aqueous dispersion comprising 0.02% by weight of active compound.

VIII. 20 parts by weight of a compound according to the invention are mixed well with 3 parts by weight of the sodium salt of diisobutylnaphthalene-α-sulfonic acid, 17 parts by weight of the sodium salt of a lignosulfonic acid from a sulfite waste liquor and 60 parts by weight of pulverulent silica gel, and ground in a hammer mill. The mixture is finely dispersed in 20,000 parts by weight of water, affording a spray liquor comprising 0.1% by weight of active compound.

The active compounds can be applied as such, in the form of their formulations or in the application forms prepared therefrom, for example in the form of directly sprayable solutions, powders, suspensions or dispersions, emulsions, oil dispersions, pastes, dusts, compositions for broadcasting or granules, by spraying, atomizing, dusting, broadcasting or watering. The application forms depend entirely on the intended uses; in each case they should if possible ensure finest distribution of the active compounds according to the invention.

Aqueous use forms can be prepared from emulsion concentrates, pastes or wettable powders (spray powders, oil dispersions) by addition of water. To prepare emulsions, pastes or oil dispersions, the substances can be homogenized in water as such or dissolved in an oil or solvent, by means of wetting agents, tackifiers, dispersants or emulsifiers. However, concentrates comprising active compound, wetting agent, tackifier, dispersant or emulsifier and possibly solvent or oil which are suitable for dilution with water can also be prepared.

The active compound concentrations in the ready-to-use preparations can be varied over a relatively wide range. In general, they are from 0.0001 to 10%, preferably from 0.01 to 1%.

It is also possible to use the active compounds with good success in the ultra-low-volume process (ULV), it being possible to apply formulations comprising more than 95% by weight of active compound or even the active compound without additives.

It is possible to admix oils of various types, herbicides, fungicides, other pesticides, or bactericides with the active compounds, even, if appropriate, immediately prior to application (tank mix). These agents may be admixed with the compositions according to the invention at a weight ratio from 1:10 to 10:1.

The compounds according to the invention in the use form as fungicides may also be present together with other active compounds, for example with herbicides, insecticides, growth regulators, fungicides or else with fertilizers. In many cases, a mixture of the compounds I or of the compositions comprising them in the use form as fungicides with other fungicides results in a widened fungicidal spectrum of activity.

The following list of fungicides, together with which the compounds according to the invention can be used, is intended to illustrate the possible combinations, but not to impose any limitation:

sulfur, dithiocarbamates and their derivatives, such as iron(III) dimethyldithiocarbamate, zinc dimethyldithiocarbamate, zinc ethylenebisdithiocarbamate, manganese ethylenebisdithiocarbamate, manganese zinc ethylenediaminebisdithiocarbamate, tetramethylthiuram disulfides, ammonia complex of zinc (N,N-ethylenebisdithiocarbamate), ammonia complex of zinc (N,N'-propylenebisdithiocarbamate), zinc (N,N'-propylenebisdithiocarbamate), N,N'-polypropylenebis (thiocarbamoyl)disulfide;

nitro derivatives, such as dinitro(1-methylheptyl)phenyl crotonate, 2-sec-butyl-4,6-dinitrophenyl-3,3-dimethyl acrylate, 2-sec-butyl-4,6-dinitrophenylisopropyl carbonate, diisopropyl 5-nitroisophthalate;

heterocyclic substances, such as 2-heptadecyl-2-imidazoline acetate, 2,4-dichloro-6-(o-chloroanilino)-s-triazine, O,O-diethyl phthalimidophosphonothioate, 5-amino-1-[bis(dimethylamino)phosphinyl]-3-phenyl-1,2,4-triazole, 2,3-dicyano-1,4-dithioanthraquinone, 2-thio-1,3-dithiolo[4,5-b]quinoxaline, methyl 1-(butylcarbamoyl)-2-benzimidazolecarbamate, 2-methoxycarbonylaminobenzimidazole, 2-(furyl-(2)) benzimidazole, 2-(thiazolyl)-(4))benzimidazole, N-(1, 1,2,2-tetrachloroethylthio)tetrahydrophthalimide, N-trichloromethylthiotetrahydrophthalimide, N-trichloromethylthiophthalimide, N-dichlorofluoromethylthio-N',N'-dimethyl-N-phenylsulfuric diamide, 5-ethoxy-3-trichloromethyl-1, 2,3-thiadiazole, 2-thiocyanatomethylthiobenzothiazole, 1,4-dichloro-2, 5-dimethoxybenzene, 4-(2-chlorophenylhydrazono)-3-methyl-5-isoxazolone, pyridine 2-thio-1-oxide, 8-hydroxyquinoline or its copper salt, 2,3-dihydro-5-carboxanilido-6-methyl-1,4-oxathiine, 2,3-dihydro-5-carboxanilido-6-methyl-1,4-oxathiine-4, 4-dioxide, 2-methyl-5,6-dihydro-4H-pyran-3-carboxanilide, 2-methylfuran-3-carboxanilide, 2,5-dimethylfuran-3-carboxanilide, 2,4,5-trimethylfuran-3-carboxanilide, N-cyclohexyl-2,5-dimethylfuran-3-carboxamide, N-cyclohexyl-N-methoxy-2,5-dimethylfuran-3-carboxamide, 2-methylbenzanilide, 2-iodobenzanilide, N-formyl-N-morpholine 2,2,2-trichloroethyl acetal, piperazine-1,4-diyl-bis-(1-(2,2,2-trichloroethyl) formamide, 1-(3,4-dichloroanilino)-1-formylamino-2, 2,2-trichloroethane, 2,6-dimethyl-N-tridecylmorpholine or its salts, 2,6-dimethyl-N-cyclododecylmorpholine or its salts, N-[3-(p-tert-butylphenyl)-2-methylpropyl]-cis-2,6-dimethylmorpholine, N-[3-(p-tert-butylphenyl)-2-methylpropyl]piperidine, 1-[2-(2,4-dichlorophenyl)-4-ethyl-1,3-dioxolan-2-ylethyl]-1H-1,2,4-triazole, 1-[2-(2,4-dichlorophenyl)-4-n-propyl-1,3-dioxolan-2-ylethyl]-1H-1,2,4-triazole, N-(n-propyl)-N-(2,4,6-trichlorophenoxyethyl)-N'-imidazolylurea, 1-(4-chlorophenoxy)-3,3-dimethyl-1-(1H-1,2,4-triazol-1-yl)-2-butanone, 1-(4-chlorophenoxy)-3,3-dimethyl-1-(1H-1,2,4-triazol-1-yl)-2-butanol, (2RS,3RS)-1-[3-(2-chlorophenyl)-2-(4-fluorophenyl)oxiran-2-ylmethyl]-1H-1,2,4-triazole, α-(2-chlorophenyl)-α-(4-chlorophenyl)-5-pyrimidinemethanol, 5-butyl-2-dimethylamino-4-hydroxy-6-methylpyrimidine, bis(p-chlorophenyl)-3-pyridinemethanol, 1,2-bis(3-ethoxycarbonyl-2-thioureido)benzene, 1,2-bis(3-methoxycarbonyl-2-thioureido)benzene, strobilurins such as methyl E-methoxyimino-[α-(o-tolyloxy)-o-tolyl]acetate, methyl E-2-{2-[6-(2-cyanophenoxy)pyrimidin-4-yloxy]phenyl}-3-methoxyacrylate, N-methyl-E-methoxyimino-[α-(2-phenoxyphenyl)]acetamide, N-methyl-E-methoxyimino-[α-(2,5-dimethylphenoxy)-o-tolyl] acetamide, anilinopyrimidines, such as N-(4,6-dimethylpyrimidin-2-yl)aniline, N-[4-methyl-6-(1-propinyl)pyrimidin-2-yl] aniline, N-[4-methyl-6-cyclopropylpyrimidin-2-yl] aniline, phenylpyrroles such as 4-(2,2-difluoro-1,3-benzodioxol-4-yl)pyrrole-3-carbonitrile, cinnamides, such as 3-(4-chlorophenyl)-3-(3,4-dimethoxyphenyl)acryloyl]morpholine, and a variety of fungicides, such as dodecylguanidine acetate, 3-[3-(3,5-dimethyl-2-oxycyclohexyl)-2-hydroxyethyl]glutarimide, hexachlorobenzene, methyl-N-(2,6-dimethylphenyl)-N-(2-furoyl)-DL-alaninate, DL-N-(2,6-dimethylphenyl)-N-(2'-methoxyacetyl) alanine methyl ester, (N-(2,6-dimethylphenyl)-N-chloroacetyl-D,L-2-aminobutyrolactone, DL-N-(2,6-dimethylphenyl)-N-(phenylacetyl)alanine methyl ester, 5-methyl-5-vinyl-3-(3,5-dichlorophenyl)-2,4-dioxo-1,3-oxazolidine, 3-(3,5-dichlorophenyl)-5-methyl-5-methoxymethyl-1,3-oxazolidine-2,4-dione, 3-(3,5-dichlorophenyl)-1-isopropylcarbamoylhydantoin, N-(3,5-dichlorophenyl)-1,2-dimethylcyclopropane-1,2-dicarboximide, 2-cyano-[N-(ethylaminocarbonyl)-2-methoximino]acetamide, 1-[2-(2,4-dichlorophenyl) pentyl]-1H-1,2,4-triazole, 2,4-difluoro-α-(1H-1,2,4-triazolyl-1-methyl)benzhydryl alcohol, N-(3-chloro-2,6-dinitro-4-trifluoromethylphenyl)-5-trifluoromethyl-3-chloro-2-aminopyridine, 1-((bis(4-fluorophenyl) methylsilyl)methyl)-1H-1,2,4-triazole.

SYNTHESIS EXAMPLES

The procedures given in the Synthesis Examples below were used to prepare further compounds I by appropriate modification of the starting materials. The compounds obtained in this manner are listed in the tables which follow, together with physical data.

Example 1

2,4-Dihydro-5-methoxy-2-methyl-4-{2-[1-(4-fluorophenyl)-1,2,4-triazolyl-3-]oxymethylphenyl}-3H-1,2,4-triazol-3-one [J-1]

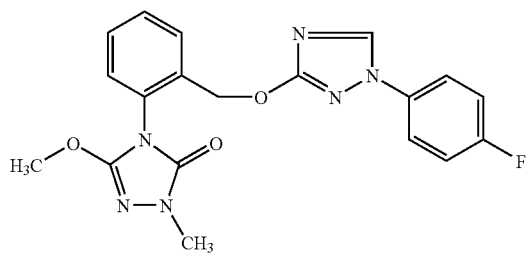

A mixture of 0.6 g (3 mmol) of (4-fluorophenyl)-3-hydroxytriazole in 15 ml of dimethylformamide was mixed with 0.1 g (3.6 mmol) of sodium hydride and stirred at 20 to 25° C. for about 5 min. 1 g (3.3 mmol) of 4-(2-bromomethylphenyl)-2,4-dihydro-5-methoxy-2-methyl-3H-1,2,4-triazol-3-one [WO-A 95/14,009] was subsequently added and the mixture was stirred at 20 to 25° C. for about 14 hours. Water was added, and the aqueous phase was extracted with methyl tert-butyl ether. The combined organic phases were extracted with water, dried and concentrated. Silica gel chromatography of the residue using cyclohexane/ethyl acetate mixtures gave 0.55 g of the title compound as a light yellow solid of m.p. 137–139° C.

¹H-NMR (CDCl₃): 3.45 (s, 3H); 3.95 (s, 3H); 5.4 (s, 2H); 7.1–7.3 (m, 3H); 7.45 (m, 2H); 7.55 (m, 2H); 7.75 (d, br, 1H); 8.15 ppm (s, 1H).

Example 2

2,5-Dihydro-2-methyl-5-{2-[1-(4-fluorophenyl) pyrazol-3-yl]oxymethylphenyl}tetrazolone [I-3]

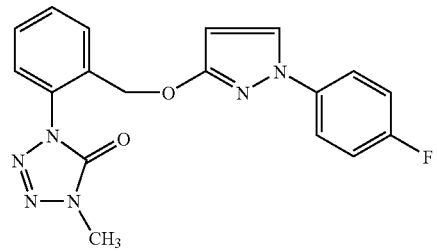

A solution of 1.36 g (7 mmol) of 1-(4-fluorophenyl)-3-hydroxypyrazole in 25 ml of anhydrous dimethylformamide (DMF) was admixed with 0.18 g of sodium hydride. The mixture was stirred at 20–25° C. for approximately one hour, a solution of 1.88 g (7 mmol) of 2,5-dihydro-2-methyl-5-(2-bromomethylphenyl)tetrazolone [WO-A 96/36229] in 15 ml of anhydrous DMF was added and the solution was stirred at 20–25° C. for a further 14 hours. The solution was diluted with 300 ml of dilute NaCl solution and extracted with methyl tert-butyl ether (MTBE) and the combined organic phases were then washed with water and dried. The solvent was distilled off and the residue was subjected to silica gel chromatography (cyclohexan/MTBE 1:1), giving 1.8 g of the title compound in the form of bright yellow crystals of m.p. 89–93° C.

Example 3

2,4-Dihydro-2,5-dimethyl-4-{2-[1-(4-chlorophenyl) pyrazol-3-yl]oxymethylphenyl}-3H-1,2,4-triazol-3-one [I-46]

Example 3a

2-[1-(4-Chlorophenyl)pyrazol-3-yl]oxymethylaniline

At 20–25° C. and a hydrogen pressure of 20 bar, a mixture of 30 g (90 mmol) of 2-[1-(4-chlorophenyl)pyrazol-3-yl] oxymethylnitrobenzene and 2 g of platinum on activated carbon (5%) in 200 ml of ethyl acetate was hydrogenated with stirring for approximately 20 hours. The mixture was filtered through Al₂O₃ and the solvent was removed from the filtrate by distillation, giving 23.3 g of the aniline as yellow crystals of m.p. 81–83° C.

¹H NMR (CDCl₃; δ in ppm): 7.65 (d, 1H); 7.5 (d, 2H); 7.35 (d, 2H); 7.25 (d, 1H); 7.15 (t, br, 1H); 6.7 (m, 2H); 5.9 (d, 1H); 5.25 (s, 2H); 4.15 (s, br, 2H).

Example 3b

Phenyl 2-[1-(4-Chlorophenyl)pyrazol-3-yl]oxymethyl Carbamate

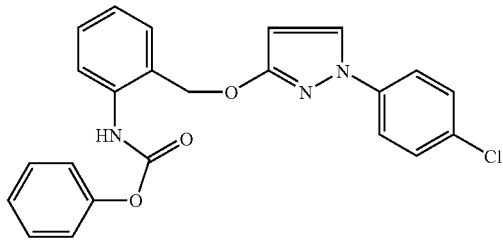

A mixture of the aniline of Example 3a and 12 g (0.15 mol) of pyridine in 200 ml of methylene chloride was admixed with 16 g (0.1 mol) of phenyl chloroformate at 0C, and the mixture was then stirred at 20–25° C. for approximately 1.5 hours. The mixture was washed with dilute hydrochloric acid and water and dried, and the solvent was distilled off. Digestion of the residue in diosopropyl ether gave 41 g of the title compound as bright yellow crystals of m.p. 143–144° C.

$^1$H NMR (CDCl$_3$; δ in ppm): 8.95 (s, br, 1H); 7.95 (d, br, 2H); 7.65 (d, 1H); 7.55 (d, 2H); 7.45 (d, 1H); 7.05–7.45 (m, 9H); 5.9 (d, 1H); 5.4 (s, 2H).

Example 3c

N-{2-[1-(4-Chlorophenyl)pyrazol-3-yl]oxymethylphenyl}-N'-methylsemicarbazide

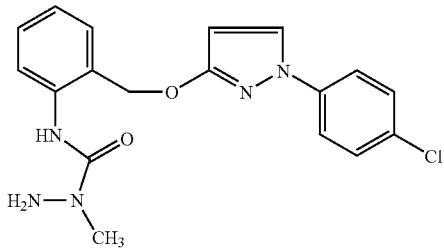

A mixture of the ester of Example 3b and 3.5 g (75 mmol) of methylhydrazine in 100 ml of methylene chloride was stirred at 20–25° C. for approximately 15 hours. The solvent was distilled off and the residue was digested in methyl tert-butyl ether (MTBE), giving 6.5 g of the title compound as bright yellow crystals of m.p. 152–154° C.

$^1$H NMR (CDCl$_3$; δ in ppm): 9.3 (s, br, 1H); 8.1 (d, 1H); 7.7 (d, 1H); 7.65 (d, 2H); 7.35 (m, 4H); 7.0 (t, 1H); 5.9 (d, 1H); 5.3 (s, 2H); 3.7 (s, 2H); 3.2 (s, 3H).

Example 3d 2,4-Dihydro-2,5-dimethyl-4-{2-[1-(4-chlorophenyl)pyrazol-3-yl]oxymethylphenyl}-3H-1,2,4-triazol-3-one [I-46]

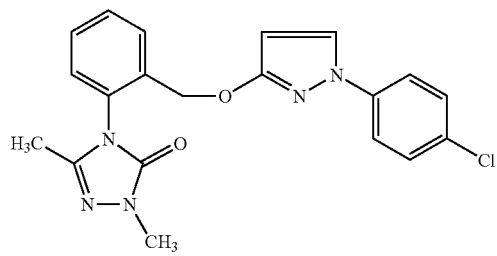

A mixture of 6 g (16 mmol) of the semicarbazide from Example 3c and a spatula tipful of p-toluenesulfonic acid in 50 ml of triethyl orthoacetate was refluxed for approximately 5 hours. The solvent was distilled off and the residue was chromatographed over silica gel (cyclohexane/ethyl acetate mixture), giving 1.9 g of the title compound as yellow crystals of m.p. 107–108° C.

$^1$H NMR (CDCl$_3$; δ in ppm): 7.7 (m, 2H); 7.5 (m, 4H); 7.35 (d, 2H); 7.2 (d, 1H); 5.85 (d, 1H); 5.25 (dd, 2H); 3.45 (s, 3H); 2,0 (s, 3H).

TABLE I

| No. | Formula | $(R^1)_n$ | $R^a$ | $R^b$ | Y | $R^2$ | $R^3$ | m.p. [° C.], IR [cm$^{-1}$] |
|---|---|---|---|---|---|---|---|---|
| I-1 | IB | H | OCH$_3$ | CH$_3$ | N | H | 4-F—C$_6$H$_4$ | 137–139 |
| I-2 | IB | H | OCH$_3$ | CH$_3$ | CH | H | 4-Cl—C$_6$H$_4$ | 1723, 1615, 1546, 1502, 1480, 1458, 1414, 1390, 1360, 744 |
| I-3 | IC | H | — | CH$_3$ | CH | H | 4-Cl—C$_6$H$_4$ | 89–93 |
| I-4 | IB | H | OCH$_3$ | CH$_3$ | CH | H | 3,4-Cl$_2$—C$_6$H$_4$ | 120–123 |
| I-5 | IB | H | Cl | CH$_3$ | CH | H | 4-CH$_3$—C$_6$H$_4$ | 146–149 |
| I-6 | IB | H | OCH$_3$ | CH$_3$ | CH | H | 4-CH$_3$—C$_6$H$_4$ | 106–108 |
| I-7 | IB | H | Cl | CH$_3$ | CH | H | 2-CH$_3$-pyridyl-6 | 115–118 |
| I-8 | IB | H | OCH$_3$ | CH$_3$ | CH | H | 2-CH$_3$-pyridyl-6 | 1725, 1615, 1581, 1547, 1505, 1480, 1466, 1414, 1390, 1360 |
| I-9 | IB | H | Cl | CH$_3$ | CH | H | 4-OC$_2$H$_5$—C$_6$H$_4$ | 128–135 |

TABLE I-continued

| No. | Formula | $(R^1)_n$ | $R^a$ | $R^b$ | Y | $R^2$ | $R^3$ | m.p. [°C.], IR [cm$^{-1}$] |
|---|---|---|---|---|---|---|---|---|
| I-10 | IB | H | OCH$_3$ | CH$_3$ | CH | H | 4-OC2H5—C6H4 | 1723, 1615, 1543, 1516, 1481, 1457, 1414, 1392, 1247, 1050 |
| I-11 | IB | H | Cl | CH$_3$ | CH | H | 3-Cl—C$_6$H$_4$ | 104–109 |
| I-12 | IB | H | OCH$_3$ | CH$_3$ | CH | H | 3-Cl—C$_6$H$_4$ | 116–118 |
| I-13 | IB | H | Cl | CH$_3$ | CH | H | 2-Cl—C$_6$H$_4$ | 1728, 1545, 1495, 1476, 1452, 1396, 1360, 761, 737, 621 |
| I-14 | IB | H | OCH$_3$ | CH$_3$ | CH | H | 2-Cl—C$_6$H$_4$ | 1725, 1615, 1546, 1495, 1477, 1452, 1414, 1361, 761, 743 |
| I-15 | IB | H | Cl | CH$_3$ | CH | H | 2,4-F$_2$—C$_6$H$_4$ | 100–103 |
| I-16 | IB | H | OCH$_3$ | CH$_3$ | CH | H | 2,4-F$_2$—C$_6$H$_4$ | 1725, 1615, 1550, 1517, 1482, 1457, 1446, 1415, 1270, 970 |
| I-17 | IB | H | Cl | CH$_3$ | CH | H | 3-Cl-pyridyl-6 | 85–94 |
| I-18 | IB | H | OCH$_3$ | CH$_3$ | CH | H | 3-Cl-pyridyl-6 | 121–129 |
| I-19 | IB | H | Cl | CH$_3$ | CH | H | 3-CF$_3$—C$_6$H$_4$ | 111–117 |
| I-20 | IB | H | OCH$_3$ | CH$_3$ | CH | H | 3-CF$_3$—C$_6$H$_4$ | 1717, 1613, 1556, 1507, 1477, 1455, 1357, 1332, 1170, 1115 |
| I-21 | IB | H | Cl | CH$_3$ | CH | H | 4-Br—C$_6$H$_4$ | 1726, 1546, 1499, 1480, 1458, 1421, 1392, 1358, 1076, 935 |
| I-22 | IB | H | OCH$_3$ | CH$_3$ | CH | H | 4-Br—C$_6$H$_4$ | 1724, 1615, 1547, 1499, 1480, 1457, 1414, 1389, 1360, 1077 |
| I-23 | IB | H | Cl | CH$_3$ | CH | H | 2,4-Cl$_2$—C$_6$H$_4$ | 1728, 1546, 1496, 1475, 1458, 1417, 1397, 1358, 1059, 763 |
| I-24 | IB | H | OCH$_3$ | CH$_3$ | CH | H | 2,4-Cl$_2$—C$_6$H$_4$ | 1725, 1615, 1547, 1496, 1477, 1414, 1389, 1359, 1321, 744 |
| I-25 | IB | H | Cl | CH$_3$ | CH | H | C$_2$H$_5$ | 1727, 1538, 1490, 1459, 1397, 1380, 1365, 765, 737, 621 |
| I-26 | IB | H | OCH$_3$ | CH$_3$ | CH | H | C$_2$H$_5$ | 1724, 1615, 1536, 1505, 1489, 1458, 1414, 1388, 1321, 743 |
| I-27 | IB | H | Cl | CH$_3$ | C(CH$_3$) | H | 4-CH$_3$—C$_6$H$_4$ | 119–130 |
| I-28 | IB | H | OCH$_3$ | CH$_3$ | C(CH$_3$) | H | 4-CH$_3$—C$_6$H$_4$ | 1725, 1615, 1519, 1506, 1480, 1457, 1414, 1361, 1199, 941 |
| I-29 | IB | H | Cl | CH$_3$ | C(CH$_3$) | H | 2,4-Cl$_2$—C$_6$H$_4$ | 81–85 |
| I-30 | IB | H | OCH$_3$ | CH$_3$ | C(CH$_3$) | H | 2,4-Cl$_2$—C$_6$H$_4$ | 141–145 |
| I-31 | IB | H | Cl | CH$_3$ | C(CH$_3$) | H | C$_6$H$_5$ | 1729, 1599, 1540, 1500, 1466, 1398, 1363, 1197, 763, 756 |
| I-32 | IB | H | OCH$_3$ | CH$_3$ | C(CH$_3$) | H | C$_6$H$_5$ | 134–137 |
| I-33 | IB | H | Cl | CH$_3$ | CCl | H | 4-CH$_3$—C$_6$H$_4$ | 130–133 |

TABLE I-continued

| No. | Formula | $(R^1)_n$ | $R^a$ | $R^b$ | Y | $R^2$ | $R^3$ | m.p. [° C.], IR [cm$^{-1}$] |
|---|---|---|---|---|---|---|---|---|
| I-34 | IB | H | OCH$_3$ | CH$_3$ | CCl | H | 4-CH$_3$—C$_6$H$_4$ | 1723, 1615, 1554, 1510, 1479, 1457, 1414, 1390, 1361, 1118 |
| I-35 | IB | H | Cl | CH$_3$ | N | H | 4-Cl—C$_6$H$_4$ | 1726, 1544 1500, 1480, 1458, 1397, 1330, 1242, 1093, 974 |
| I-36 | IB | H | OCH$_3$ | CH$_3$ | N | H | 4-Cl—C$_6$H$_4$ | 1706, 1619, 1603, 1547, 1486, 1477, 1336, 1326, 1083, 980 |
| I-37 | IB | H | Cl | CH$_3$ | N | H | 2,4-Cl$_2$—C$_6$H$_4$ | 1726, 1544, 1494, 1477, 1457, 1396, 1331, 1274, 1065, 994 |
| I-38 | IB | H | OCH$_3$ | CH$_3$ | N | H | 2,4-Cl$_2$—C$_6$H$_4$ | 1723, 1616, 1545, 1479, 1457, 1414, 1388, 1330, 1066, 974 |
| I-39 | IB | H | Cl | CH$_3$ | N | H | 3,4-(CH$_3$)$_2$—C$_6$H$_3$ | 1728, 1542, 1505, 1481, 1458, 1397, 1330, 1243, 1065, 994 |
| I-40 | IB | H | OCH$_3$ | CH$_3$ | N | H | 3,4-(CH$_3$)$_2$—C$_6$H$_3$ | 127–131 |
| I-41 | IB | H | Cl | CH$_3$ | N | H | 4-CF$_3$—C$_6$H$_4$ | 134–145 |
| I-42 | IB | H | OCH$_3$ | CH$_3$ | N | H | 4-CF$_3$—C$_6$H$_4$ | 145–149 |
| I-43 | IB | H | Cl | CH$_3$ | N | CH$_3$ | 2,4-Cl$_2$—C$_6$H$_4$ | 1728, 1540, 1488, 1457, 1419, 1396, 1349, 1274, 1018, 994 |
| I-44 | IB | H | OCH$_3$ | CH$_3$ | N | CH$_3$ | 2,4-Cl$_2$—C$_6$H$_4$ | 1724, 1616, 1541, 1502, 1480, 1457, 1415, 1389, 1350, 1068 |
| I-45 | IA | H | OCH$_3$ | CH$_3$ | CH | N | 4-Cl—C$_6$H$_4$ | 1641, 1603, 1546, 1502, 1481, 1400, 1383, 1359, 1028, 936 |
| I-46 | IB | 6-CH$_3$ | OCH$_3$ | CH$_3$ | CH | H | 4-Cl—C$_6$H$_4$ | 1722, 1613, 1546, 1502, 1488, 1502, 1425, 1413, 1390, 1358 1070 |
| I-47 | IB | H | CH$_3$ | CH$_3$ | CH | H | 4-Cl—C$_6$H$_4$ | 107–109 |
| I-48 | IB | 6-CH$_3$ | H | CH$_3$ | CH | H | 4-Cl—C$_6$H$_4$ | 126–128 |
| I-49 | IB | H | H | CH$_3$ | CH | H | 4-Cl—C$_6$H$_4$ | 130–132 |
| I-50 | IB | 6-CH$_3$ | CH$_3$ | CH$_3$ | CH | H | 4-Cl—C$_6$H$_4$ | 120–124 |

Examples of the Action Against Harmful Fungi

The fungicidal action of the compounds of the formula I was demonstrated by the following experiments:

The active compounds, separately or together, were formulated as a 10% emulsion in a mixture of 63% by weight of cyclohexanone and 27% by weight of emulsifier and diluted with water to the desired concentration.

Use Example 1

Activity Against *Plasmopara viticola*

Leaves of potted vines of the variety "Mller-Thurgau" were sprayed with an aqueous active compound preparation prepared from a stock solution of 10% of active compound, 63% of cyclohexanone and 27% of emulsifier until dripping wet. To be able to assess the long-term activity of the substances, the plants were kept for 7 days in the greenhouse after the spray coating had dried on. Only then were the leaves inoculated with an aqueous zoospore suspension of *Plasmopara viticola*. The vines were then first kept in a chamber saturated with water vapor at 24° C. for 48 hours, and then in a greenhouse at 20–30° C. for 5 days. The plants were then kept for a further 16 hours in a chamber of high atmospheric humidity to stimulate sporalation of the fungus. The extent of the infection at the undersides of the leaves was then assessed visually.

In this test, the plants which had been treated with 16 ppm of the compounds No. I-2, I-4, I-6, I-8, I-10, I-12, I-16, I-18, I-20, I-22, I-24, I-28, I-32, I-38 and I-44 showed a maximum infection of 15%, whereas infection levels in the untreated plants were 75%.

Use Example 2

Activity Against *Puccinia recondita* on Wheat (Wheat Leaf Rust)

Leaves of potted wheat seedlings of the variety "Frühgold" were dusted with spores of the wheat leaf rust (*Puccinia recondite*).

Thereafter, the pots were kept in a chamber of high atmospheric humidity (90 to 95%) and 20 to 22° C. for 24 hours. During this time, the spores germinated and the germinal tubials penetrated into the leaf tissue. The next day, the infected plants were sprayed with an aqueous active compound formulation to runoff point. After the spray coating had dried on, the test plants were cultivated for 7 days in a greenhouse at 20–22° C. and 65–70% relative atmospheric humidity. Thereafter, the extent of the rust fungus development on the leaves was determined.

In this test, plants which had been treated with 16 ppm of the compounds No. I-2, I-4, I-6, I-16, I-22, I-24, I-28, I-32 and I-38 showed an infection of not more than 15%, whereas infection levels in the untreated plants were 80%.

Use Example 3

Activity Against *Pyricularia oryzae* (Protective)

Leaves of potted rice seedlings of the variety "Tai-Nong 67" were sprayed with an aqueous active compound formulation to runoff point. The next day, the plants were inoculated with an aqueous spore suspension of *Pyricularia oryzae*. The test plants were subsequently kept for 6 days in conditioning chambers at 22–24° C. and 95–99% relative atmospheric humidity. Thereafter, the extent of development of the disease on the leaves was determined visually.

In this test, plants which had been treated with 16 ppm of the compounds No. I-2, I-6, I-12, I-16, I-18, I-20, I-21, I-22, I-23, I-24, I-28, I-30, I-32 and I-40 showed an infection of 0 to 15% whereas infection levels in the untreated plants were 90%.

Examples of Action Against Animal Pests

The action of the compounds of the formula I against animal pests was demonstrated by the following experiments:

The active compounds were formulated
a. as a 0.1% solution in acetone or
b. as a 10% emulsion in a mixture of 70% by weight of cyclohexanone, 20% by weight of Nekanil® LN (Lutensol® AP6, wetting agent based on ethoxylated alkyl phenols having emulsifying and dispersing action) and 10% by weight of Wettol® EM (nonionic emulsifier based on ethoxylated castor oil)
and diluted in the case of a. with acetone and in the case of b. with water to give the desired concentration.

After the experiments had ended, in each case the lowest concentration was determined at which the compounds still caused an 80 to 100% inhibition or mortality in comparison with untreated control experiments (critical or minimal is concentration).

We claim:
1. A compound of formula I

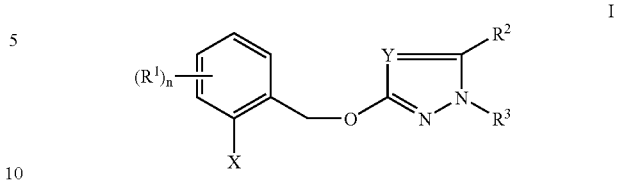

wherein
X is a group B

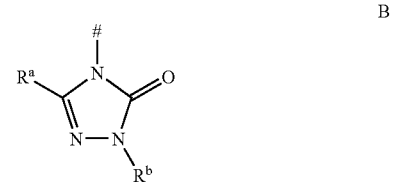

wherein
# denotes the bond with the phenyl ring,
$R^a$ is hydrogen, halogen, $C_1$–$C_4$-alkyl or $C_1$–$C_4$-alkoxy, and
$R^b$ is $C_1$–$C_4$-alkyl;
Y is $CR^c$, wherein $R^c$ is hydrogen, halogen or $C_1$–$C_4$-alkyl;
n is 0, 1, 2, 3 or 4, wherein the substituents $R^1$ are identical or different when n is 2, 3 or 4;
$R^1$ is nitro, cyano, halogen,
  is unsubstituted or substituted $C_1$–$C_6$-alkyl, or unsubstituted or substituted $C_1$–$C_4$-alkoxy, or
  is additionally, when n is 2, an unsubstituted or substituted bridge consisting of 3 carbon atoms or 4 carbon atoms, which bridge is attached to two adjacent ring atoms, and which bridge, together with the ring to which it is attached, forms a partially unsaturated or an aromatic radical;
$R^2$ is hydrogen, nitro, cyano, halogen, $C_1$–$C_4$-alkyl, $C_1$–$C_4$-haloalkyl, $C_1$–$C_4$-alkoxy, $C_1$–$C_4$-alkylthio or $C_1$–$C_4$-alkoxycarbonyl;
$R^3$ is unsubstituted or substituted $C_1$–$C_6$-alkyl, unsubstituted or substituted $C_3$–$C_6$-cycloalkyl, unsubstituted or substituted aryl;
wherein the alkyl, alkenyl or alkynyl group which is identified as being "unsubstituted or substituted" is unsubstituted, or is partially or fully halogenated, or carries, optionally in addition to halogen,
  one to three radicals selected from the group consisting of: $C_1$–$C_6$-alkoxy, $C_1$–$C_6$-haloalkoxy, $C_1$–$C_6$-alkylthio, $C_1$–$C_6$-haloalkylthio, $C_1$–$C_6$-alkylamino, di-($C_1$–$C_6$)-alkylamino, $C_2$–$C_6$-alkenyloxy, $C_2$–$C_6$-haloalkenyloxy, $C_2$–$C_6$-alkynyloxy, $C_2$–$C_6$-haloalkynyloxy, $C_3$–$C_6$-cycloalkyl, $C_3$–$C_6$-cycloalkyloxy, $C_3$–$C_6$-cycloalkenyl and $C_3$–$C_6$-cycloalkenyloxy,
  one unsubstituted or substituted mono- or dinuclear aromatic ring system consisting of carbon ring members which is attached to the alkyl, alkenyl or alkynyl group directly or is attached thereto via an oxygen atom (—O—), a sulfur atom (—S—) or via an amino group (—$NR^a$—), and
wherein the cyclic saturated, unsaturated or aromatic group which is identified as being "unsubstituted or substituted" is unsubstituted, or is partially or fully halogenated, or carries, optionally in addition to halogen, one to four radicals selected from the group consisting of: cyano, nitro, hydroxy, amino, carboxyl, aminocarbonyl, $C_1-C_6$-alkyl, $C_1-C_6$-haloalkyl, alkenyl, haloalkenyl, alkenyloxy, haloalkenyloxy, alkynyl, haloalkynyl, alkynyloxy, haloalkynyloxy, $C_1-C_6$-alkoxy, $C_1-C_6$-haloalkoxy, $C_1-C_6$-alkylthio, $C_1-C_6$-haloalkylthio, $C_1-C_6$-alkylamino, di($C_1-C_6$-alkyl)amino, $C_1-C_6$-alkylcarbonyl, $C_1-C_6$-alkoxycarbonyl, $C_1-C_6$-alkylcarbonyloxy, $C_1-C_6$-alkylaminocarbonyl, di($C_1-C_6$-alkyl)aminocarbonyl, $C_1-C_6$-alkylcarbonylamino, $C_1-C_6$-alkoxycarbonylamino, $C_1-C_6$-alkylcarbonyl-N—$C_1-C_6$-alkylamino and $C_1-C_6$-alkoxycarbonyl-N—$C_1-C_6$-alkylamino, one to three radicals selected from the group consisting of: $C_3-C_{12}$-cycloalkyl, $C_3-C_{12}$-cycloalkoxy, $C_3-C_{12}$-cycloalkylthio, $C_3-C_{12}$-cycloalkylamino, $C_3-C_{12}$-cycloalkyl-N—$C_1-C_6$-alkylamino, aryl, aryloxy, arylthio, arylamino, aryl-N—$C_1-C_6$-alkylamino, aryl-$C_1-C_6$-alkoxy, aryl-$C_1-C_6$-alkylthio, aryl-$C_1-C_6$-alkylamino and aryl-$C_1-C_6$-alkyl-N—$C_1-C_6$-alkylamino, one or two radicals selected from the group consisting of: formyl, $CR^{iii}=NOR^{iv}$, where $R^{iii}$ is hydrogen, $C_1-C_6$-alkyl, $C_3-C_8$-cycloalkyl or aryl, and $R^{iv}$ is $C_1-C_6$-alkyl, $C_3-C_8$-alkenyl, $C_3-C_8$-haloalkenyl, $C_3-C_8$-alkynyl and aryl-$C_1-C_6$-alkyl, $NR^v$—CO—D—$R_{vi}$, where $R^v$ is hydrogen, hydroxy, $C_1-C_6$-alkyl, $C_2-C_6$-alkenyl, $C_2-C_6$-alkynyl, $C_1-C_6$-alkoxy, $C_2-C_6$-alkenyloxy, $C_2-C_6$-alkynyloxy, $C_1-C_6$-alkoxy-$C_1-C_6$-alkyl, $C_1-C_6$-alkoxy-$C_1-C_6$-alkoxy and $C_1-C_6$-alkoxycarbonyl, $R^{vi}$ is hydrogen, $C_1-C_6$-alkyl, $C_2-C_6$-alkenyl, $C_2-C_6$-alkynyl, $C_3-C_6$-cycloalkyl, $C_3-C_6$-cycloalkenyl, aryl and aryl-$C_1-C_6$-alkyl, and D is a direct bond, oxygen or nitrogen, where the nitrogen carries one of the groups mentioned under $R_{vi}$, one $C_3-C_5$-alkylene, $C_3-C_5$-alkenylene, oxy-$C_2-C_4$-alkylene, oxy-$C_1-C_3$-alkylenoxy, oxy-$C_2-C_4$-alkenylene, oxy-$C_2-C_4$-alkenylenoxy or butadienediyl group, which group is bonded to two adjacent ring members of the cyclic groups, and which optionally carries one to three substituents selected from the group of: $C_1-C_4$-alkyl, $C_1-C_4$-haloalkyl, $C_1-C_4$-alkoxy, $C_1-C_4$-haloalkoxy and $C_1-C_4$-alkylthio, where the aryl radicals have from 6 to 10 ring members.

2. A process for preparing the compound of formula I defined in claim 1, which comprises reacting a benzyl compound of formula II

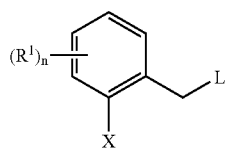

wherein L is a nucleophilically displaceable group, with a 3-hydroxypyrazole or 3-hydroxytriazole of formula III

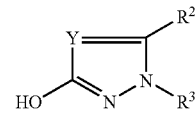

in the presence of a base.

3. A composition suitable for controlling harmful fungi, which comprises a solid or liquid carrier and an effective amount of the compound of formula I defined in claim 1.

4. A method for controlling harmful fungi, which comprises treating the fungi or materials, plants, soil or seeds to be protected from said fungi with an effective amount of the compound of formula I defined in claim 1.

5. The compound of formula I defined in claim 1, wherein $R^c$ denotes hydrogen.

6. The compound of formula I defined in claim 5, wherein $R^a$ and $R^b$ denote methyl.

7. The compound of formula I defined in claim 1, wherein $R^a$ is $C_1-C_4$-alkyl or $C_1-C_4$-alkoxy.

8. The compound of formula I defined in claim 1, wherein $R^b$ is methyl.

9. The compound of formula I defined in claim 1, wherein the cyclic saturated, unsaturated or aromatic group which is identified as being "unsubstituted or substituted" is unsubstituted, or is partially or fully halogenated, or carries, optionally in addition to halogen, one to three radicals selected from the group consisting of: cyano, nitro, hydroxy, amino, carboxyl, aminocarbonyl, $C_1-C_4$-alkyl, $C_1-C_4$-haloalkyl, $C_2-C_4$-alkenyl, $C_2-C_4$-haloalkenyl, $C_2-C_4$-alkenyloxy, $C_2-C_4$-haloalkenyloxy, $C_2-C_4$-alkynyl, $C_2-C_4$-haloalkynyl, $C_2-C_4$-alkynyloxy, $C_2-C_4$-haloalkynyloxy, $C_1-C_4$-alkoxy, $C_1-C_4$-haloalkoxy, $C_1-C_4$-alkylthio, $C_1-C_4$-haloalkylthio, $C_1-C_4$-alkylamino, di($C_1-C_4$-alkyl)amino, $C_1-C_4$-alkylcarbonyl, $C_1-C_4$-alkoxycarbonyl, $C_1-C_4$-alkylcarbonyloxy, $C_1-C_4$-alkylaminocarbonyl, di($C_1-C_4$-alkyl)aminocarbonyl, $C_1-C_4$-alkylcarbonylamino, $C_1-C_4$-alkoxycarbonylamino, $C_1-C_4$-alkylcarbonyl-N—$C_1-C_4$-alkylamino and $C_1-C_4$-alkoxycarbonyl-N—$C_1-C_4$-alkylamino, one radical selected from the group consisting of: $C_3-C_8$-cycloalkyl, $C_3-C_8$-cycloalkoxy, $C_3-C_8$-cycloalkylthio, $C_3-C_8$-cycloalkylamino, $C_3-C_8$-cycloalkyl-N—$C_1-C_6$-alkylamino, phenyl, phenoxy, phenylthio, phenylamino, phenyl-N—$C_1-C_4$-alkylamino, phenyl-$C_1-C_4$-alkoxy, phenyl-$C_1-C_4$-alkylthio, phenyl-$C_1-C_4$-alkylamino and phenyl-$C_1-C_4$-alkyl-N—$C_1-C_4$-alkylamino, one radical selected from the group consisting of: formyl, $CR^{iii}=NOR_{iv}$, where $R^{iii}$ is hydrogen, $C_1-C_4$-alkyl, $C_3-C_6$-cycloalkyl or phenyl, and $R^{iv}$ is $C_1-C_4$-alkyl, $C_3-C_6$-alkenyl, $C_3-C_6$-haloalkenyl, $C_3-C_6$-alkynyl and phenyl-$C_1-C_4$-alkyl, $NR^v$—CO—D—$R^{vi}$, where $R^v$ is hydrogen, hydroxy, $C_1-C_6$-alkyl, $C_2-C_6$-alkenyl, $C_2-C_6$-alkynyl, $C_1-C_6$-alkoxy, $C_2-C_6$-alkenyloxy, $C_2-C_6$-alkynyloxy, $C_1-C_6$-alkoxy-$C_1-C_6$-alkyl, $C_1-C_6$-alkoxy-$C_1-C_6$-alkoxy and $C_1-C_6$-alkoxycarbonyl, $R^{vi}$ is hydrogen, $C_1-C_6$-alkyl, $C_2-C_6$-alkenyl, $C_2-C_6$-alkynyl, $C_3-C_6$-cycloalkyl, $C_3-C_6$-cycloalkenyl, phenyl and phenyl-$C_1-C_6$-alkyl, and D is a direct bond, oxygen or nitrogen, where the nitrogen carries one of the groups mentioned under $R^{vi}$, one $C_3-C_5$-alkylene, $C_3-C_5$-alkenylene, oxy-$C_2-C_4$-alkylene, oxy-$C_1-C_3$-alkylenoxy, oxy-$C_2-C_4$- alkenylene, oxy-$C_2$–$C_4$-alkenylenoxy or butadienediyl group, which group is bonded to two adjacent ring members of the cyclic groups, and which optionally carries one or two substituents selected from the group of: $C_1$–$C_4$-alkyl, $C_1$–$C_4$-haloalkyl, $C_1$–$C_4$-alkoxy, $C_1$–$C_4$-haloalkoxy and $C_1$–$C_4$-alkylthio.

10. The compound of formula I defined in claim 1, wherein n is 0 or 1 and $R^1$ is halogen or methyl.

11. The compound of formula I defined in claim 1, wherein $R^2$ is hydrogen or $C_1$–$C_4$-alkyl.

12. The compound of formula I defined in claim 1, wherein $R^1$ is nitro, cyano, halogen, $C_1$–$C_6$-alkyl or $C_1$–$C_4$-alkoxy, $R^2$ is hydrogen, nitro, cyano, halogen, $C_1$–$C_4$-alkyl, $C_1$–$C_4$-haloalkyl, $C_1$–$C_4$-alkoxy, $C_1$–$C_4$-alkylthio or $C_1$–$C_4$-alkoxycarbonyl;

$R^3$ is unsubstituted or substituted aryl.

13. The compound of formula I defined in claim 9, wherein $R^1$ is nitro, cyano, halogen, $C_1$–$C_6$-alkyl or $C_1$–$C_4$-alkoxy, $R^2$ is hydrogen, nitro, cyano, halogen, $C_1$–$C_4$-alkyl, $C_1$–$C_4$-haloalkyl, $C_1$–$C_4$-alkoxy, $C_1$–$C_4$-alkylthio or $C_1$–$C_4$-alkoxycarbonyl;

$R^3$ is unsubstituted or substituted phenyl or benzyl.

14. The compound of formula I defined in claim 1, wherein $R^3$ is phenyl or benzyl, wherein the phenyl radical is unsubstituted, or is partially or fully halogenated, or carries, optionally in addition to halogen, one to three radicals selected from the group consisting of: cyano, nitro, $C_1$–$C_6$-alkyl, $C_1$–$C_4$-haloalkyl, $C_1$–$C_4$-alkoxy, $C_1$–$C_4$-haloalkoxy, $C_1$–$C_4$-alkoxy-$C_1$–$C_4$-alkyl, $C_3$–$C_6$-cycloalkyl, $C_1$–$C_4$-alkylcarbonyl, $C_1$–$C_4$-alkoxycarbonyl, phenyl, phenoxy and phenyl-$C_1$–$C_4$-alkoxy, where the phenyl rings in turn may be partially or fully halogenated and/or carry one to three of the following radicals: cyano, nitro, $C_1$–$C_4$-alkyl, $C_1$–$C_2$-haloalkyl, $C_1$–$C_4$-alkoxy, $C_1$–$C_2$-haloalkoxy, $C_3$–$C_6$-cycloalkyl, $C_1$–$C_4$-alkylcarbonyl and $C_1$–$C_4$-alkoxycarbonyl, one group group CR'=NOR" in which R' is hydrogen or $C_1$–$C_4$-alkyl and R" is $C_1$–$C_6$-alkyl, and/or an oxy-$C_1$–$C_3$-alkoxy bridge or an oxy-$C_1$–$C_3$-haloalkoxy bridge which is bonded to two adjacent C-atoms of the phenyl radical.

15. The process of claim 2, wherein the nucleophilically displaceable group L denotes halogen, or an alkyl or aryl sulfonate.

16. The process of claim 2, wherein the nucleophilically displaceable group L denotes chlorine, bromine, iodine, methylsulfonate, trifluoromethylsulfonate, phenylsulfonate or 4-methylphenylsulfonate.

* * * * *